US011560577B2

(12) United States Patent
Green et al.

(10) Patent No.: US 11,560,577 B2
(45) Date of Patent: *Jan. 24, 2023

(54) METHODS FOR MAKING L-GLUFOSINATE

(71) Applicant: BASF SE, Ludwigshafen (DE)

(72) Inventors: Brian Michael Green, Lutherville, MD (US); Michelle Lorraine Gradley, Canterbury (GB)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/997,133

(22) Filed: Aug. 19, 2020

(65) Prior Publication Data
US 2020/0385767 A1 Dec. 10, 2020

Related U.S. Application Data

(60) Continuation of application No. 16/287,290, filed on Feb. 27, 2019, now Pat. No. 10,781,465, which is a continuation of application No. 15/787,448, filed on Oct. 18, 2017, now Pat. No. 10,260,078, which is a division of application No. 15/445,254, filed on Feb. 28, 2017, now Pat. No. 9,834,802.

(60) Provisional application No. 62/302,421, filed on Mar. 2, 2016, provisional application No. 62/336,989, filed on May 16, 2016, provisional application No. 62/413,240, filed on Oct. 26, 2016.

(51) Int. Cl.
| | |
|---|---|
| *C12P 13/02* | (2006.01) |
| *C12P 41/00* | (2006.01) |
| *C12P 9/00* | (2006.01) |
| *C12P 13/04* | (2006.01) |
| *A01N 25/30* | (2006.01) |
| *A01N 57/20* | (2006.01) |
| *C12N 1/20* | (2006.01) |
| *C12N 9/10* | (2006.01) |

(52) U.S. Cl.
CPC .............. *C12P 13/02* (2013.01); *A01N 25/30* (2013.01); *A01N 57/20* (2013.01); *C12N 1/20* (2013.01); *C12N 9/10* (2013.01); *C12P 9/00* (2013.01); *C12P 13/04* (2013.01); *C12P 41/00* (2013.01); *C12Y 104/03003* (2013.01); *C12Y 206/01019* (2013.01)

(58) Field of Classification Search
CPC ........... C12P 13/02; C12P 41/00; C12P 13/04; C12P 9/00; C12N 1/20; C12N 9/10; C12Y 104/03003; C12Y 206/01019; A01N 57/20; A01N 25/30; A01N 57/18
See application file for complete search history.

(56) References Cited

U.S. PATENT DOCUMENTS

| | | | |
|---|---|---|---|
| 5,130,246 A | 7/1992 | Schulz et al. | |
| 5,162,212 A | 11/1992 | Schulz et al. | |
| 5,587,319 A | 12/1996 | Then et al. | |
| 5,753,470 A | 5/1998 | Then et al. | |
| 5,767,309 A | 6/1998 | Knorr et al. | |
| 5,877,013 A | 3/1999 | Liao et al. | |
| 5,919,669 A | 7/1999 | Then et al. | |
| 5,962,281 A | 10/1999 | Then et al. | |
| 6,051,408 A | 4/2000 | Bartsch et al. | |
| 6,335,186 B1 | 1/2002 | Bartsch et al. | |
| 6,936,444 B1 | 8/2005 | Bartsch | |
| 7,939,702 B2 | 5/2011 | Choi et al. | |
| 7,939,709 B2 | 5/2011 | Hawkes et al. | |
| 8,716,184 B2 | 5/2014 | Angermann et al. | |
| 8,946,507 B2 * | 2/2015 | Hawkes ............... | C12P 41/007 800/274 |
| 8,981,142 B2 | 3/2015 | Albizati et al. | |
| 9,215,868 B2 | 12/2015 | Baur et al. | |
| 9,551,018 B2 | 1/2017 | Robins et al. | |
| 9,834,802 B2 | 12/2017 | Green et al. | |
| 10,081,812 B2 | 9/2018 | Ji et al. | |
| 10,260,078 B2 * | 4/2019 | Green ..................... | C12P 41/00 |
| 2003/0022792 A1 | 1/2003 | Hacker et al. | |
| 2017/0253897 A1 | 9/2017 | Green et al. | |
| 2018/0030487 A1 | 2/2018 | Green et al. | |

FOREIGN PATENT DOCUMENTS

| | | |
|---|---|---|
| CN | 1312683 A | 9/2001 |
| CN | 101405394 A | 4/2009 |
| CN | 105567780 A | 5/2016 |

(Continued)

OTHER PUBLICATIONS

Fan et al., A novel d-mandelate dehydrogenase used in three-enzyme cascade reaction for highly efficient synthesis of non-natural chiral amino acids. J. Biotechnol., 2015, vol. 195: 67-71 (Year: 2015).*
Hanson et al., Enzymatic Synthesis of L-6-hydroxynorleucine. Bioorganic & Med. Chem., 1999, vol. 7: 2247-2252. (Year: 1999).*
Hayashi et al., A Novel Method of Amino Acids in a Cell Factory. Chapter 25, Asymmetric Synthesis and Applications of-Amino Acids, ACS Symposium Series, 2009, pp. 407-417. (Year: 2009).*

(Continued)

*Primary Examiner* — Ganapathirama Raghu
(74) *Attorney, Agent, or Firm* — Marshall, Gerstein & Borun LLP

(57) ABSTRACT

Methods for the production of L-glufosinate (also known as phosphinothricin or (S)-2-amino-4-(hydroxy(methyl) phosphonoyl)butanoic acid) are provided. The methods comprise a two-step process. The first step involves the oxidative deamination of D-glufosinate to PPO (2-oxo-4-(hydroxy(methyl)phosphinoyl)butyric acid). The second step involves the specific amination of PPO to L-glufosinate, using an amine group from one or more amine donors. By combining these two reactions, the proportion of L-glufosinate in a mixture of L-glufosinate and D-glufosinate can be substantially increased.

18 Claims, 2 Drawing Sheets

Specification includes a Sequence Listing.

(56) References Cited

FOREIGN PATENT DOCUMENTS

| | | |
|---|---|---|
| CN | 105603015 A | 5/2016 |
| CN | 106916857 A | 7/2017 |
| CN | 106978368 A | 7/2017 |
| CN | 107119084 A | 9/2017 |
| CN | 107445986 A | 12/2017 |
| CN | 107467061 A | 12/2017 |
| CN | 108342423 A | 7/2018 |
| CN | 108660167 A | 10/2018 |
| DE | 3842174 A1 | 6/1990 |
| EP | 0364275 A2 | 4/1990 |
| JP | H06245780 A | 9/1994 |
| WO | WO-2000/008938 A1 | 2/2000 |
| WO | WO-02/36742 A2 | 5/2002 |
| WO | WO-2003/072792 A2 | 9/2003 |
| WO | WO-2005/090582 A1 | 9/2005 |
| WO | WO-2016/180755 A1 | 11/2016 |
| WO | WO-2017/151573 A1 | 9/2017 |
| WO | WO-2018/108797 A1 | 6/2018 |

OTHER PUBLICATIONS

Bommarius et al., Transamination and Reductive Amination. Section 2.4, Biocatalysis, 2014, pp. 1-24, Ed., Georg Thieme Verlag KG. (Year: 2014).*

Enzyme entry: EC 1.4.1.5, Expasy, 2 pages downloaded May 25, 2022. (Year: 2022).*

Wikipedia, Glufosinate, 5 pages downloaded from https://en.wikipedia.org May 25, 2022. (Year: 2022).*

Kohls et al., Recent achievements in developing the biocatalytic toolbox for chiral amine synthesis. Current Opinion in Chemical Biology, 2014, vol. 19:180-192. (Year: 2014).*

Safety Data Sheet/Forfeit(TM) 280 Herbicide, Loveland Products Product Information, 2013, pp. 1-4, http://_msdsdiqital.com/system/files/mp_B91002.pdf.

U.S. Appl. No. 15/445,254, Non-Final Office Action, dated Jun. 21, 2017, 37 pages.

U.S. Appl. No. 15/445,254, Notice of Allowance, dated Oct. 13, 2017, 9 pages.

U.S. Appl. No. 15/787,448, Non-Final Office Action, dated Jul. 30, 2018, 9 pages.

U.S. Appl. No. 15/787,448, Notice of Allowance, dated Dec. 4, 2018, 7 pages.

AU2017227553, First Examination Report, dated Mar. 27, 2020, 3 pages.

Bartsch et al., "Stereospecific Production of the Herbicide Phosphinothricin (Glufosinate) by Transamination: Cloning, Characterization, and Overexpression of the Gene Encoding a Phosphinothricin-Specific Transaminase from *Escherichia coli, Applied Environmental Microbiology*," 1990, 56(1):7-12.

Bartsch et al., "Stereospecific Production of the Herbicide Phosphinothricin (Glufosinate): Purification of Aspartate Transaminase from *Bacillus stearothermophilus*, Cloning of the Corresponding Gene, aspC, and Application in a Coupled Transaminase Process," *Applied Environmental Microbiology*, 1996, 62(10):37943799.

Bhatia et al., "Unique Biocatalytic Approach for the Synthesis of Chirally Pure Unnatural a- and I3-amino Acids Using Novel Transaminases," *Peptide Revolution: Genomics, Proteomics & Therapeutics, Proceedings of the Eighteenth American Peptide Symposium*, ed. Michael Chorev and Tomi K. Sawyer, 2004, Jul. 19-23, 2003, pp. 47-48.

Brenda database via internet https://www.brenda-enzymes.org/search_result.php?quicksearch=I&no0fResults=10&a=9&W [2]=2.6.1&T[2]=2&V[8]=1_and linked pages, accessed Sep. 7, 2017.

Brenda database via internet https://www.brenda-enzymes.org/enzyme.php?ecno=1.4.3.3, Accessed Sep. 7, 2017.

Broun et al., Catalytic plasticity of fatty acid modification enzymes underlying chemical diversity of plant lipids. Science, 1998, vol. 282:1315-1317.

Devos et al., Practical limits of function prediction. Proteins: Structure, Function, and Genetics. 2000, vol. 41: 98-107.

EP17710654.9, Office Action, dated Jan. 16, 2020, 6 pages.

European Patent Application No. 17710654.9, Communication pursuant to Article 93(3) EPC, dated Jun. 19, 2019, 6 pages.

European Patent Office, International Searching Authority, International Application PCT/US2017/019871, International Search Report and Written Opinion dated May 9, 2017.

Hawkes et al., "D-glufosinate as a male sterility agent for hybrid seed production," *Plant Biotechnology Journal*, 2011, 9(3):301-14.

Jensen, R. et al.; "Evolutionary Recruitment of Biochemically Specialized Subdivisions of Family I with the Protein Superfamily of Aminotransferases"; *Journal ofBacteriology*; Apr. 1996; pp. 2161-2171; vol. 178, No. 8.

Khomutov, et al., "Convenient syntheses of phosphinic analogues of gamma-aminobutyric- and glutamic acids," Russian Journal of Bioorganic Chemistry, 2016, 42:672-676.

PCT/US2017/019871, International Preliminary Reporton Patentability, dated Sep. 13, 2018, 12 pages.

PCT/US2017/019871, International Search Report and Written Opinion, dated May 9, 2017, 18 pages.

Pollegioni, et al., "New biotech applications from evolved D-amino acid oxidases," Trends in Biotechnology, 2011, 29:276-283.

Schulz et al., "Stereospecific Production of the Herbicide Phosphinothricin (Glufosinate) by Transamination: Isolation and Characterization of a Phosphinothricin-Specific Transaminase from *Escherichia coli*," *Appl Environ Microbiol*, 1990, 56(1):1-6.

Seffernick et al., Melamine deaminase and Atrazine chlorohydrolase: 98 percent identical but functionally different. J. Bacteriol., 2001, vol. 183 (8): 2405-2410.

Seo et al., "Deracemization of unnatural amino acid: homoalanine using D-amino acid oxidase and co-transaminase," *Organic & Biomolecular Chemistry*, 2012, 10:2482-2485.

Takahashi, S. et al.; Bacterial d-amino acid oxidases: Recent findings and future perspectives; *Bioengineered*; Jul./Aug. 2015; pp. 237-241; vol. 6, No. 4.

UniProtKB/Swiss-prot: P22256.1: 10 pages downloaded from https://www.ncbi.nlm.nih.gov/protein/P22256 on Jun. 12, 2017.

Whisstock et al., Prediction of protein function from protein sequence. Q. Rev. Biophysics., 2003, vol. 36 (3): 307-340.

Witkowski et al., Conversion of b-ketoacyl synthase to a Malonyl Decarboxylase by replacement of the active cysteine with glutamine. Biochemistry, 1999, vol. 38: 11643-11650.

ZA2018/05680, Notice of Allowance, dated Sep. 3, 2019, 1 page.

Zeiss, "Enantioselective synthesis of L-phosphinothricin from L-methionine and L-glutamic acid via L-vinylglycine," Tetrahedron, 1992, 48:8263-8270.

NCBI Reference Sequence: WP_028002922.1, aminotransferase [Simorhizobium arboris], Jun. 12, 2014.

Boselli et al., Investigating the role of active site residues of *Rhodotorula gracilis* D-amino acid oxidase on its substrate specificity, Biochimie, 89:360-368 (2007).

Indian Patent Application No. 201817031663, Opposition under Section 25(1), Opponent: Dr. Meera Sharma, dated Jan. 7, 2022.

Nakajima et al., Enzymatic conversion of racemic methionine to the L-enantiomer, J. Chem. Soc. Chem. Commun., pp. 947-948 (1990).

Trost et al., Minimization of by-product formation during d-amino acid oxidase catalyzed racemate resolution of D/L-amino acids, J. Mol. Catalysis B: Enzymatic, 19-20:189-95 (2002).

Australian Patent Application No. 2021201498, Examination Report, dated Jun. 10, 2022.

* cited by examiner

SEQUENCE LISTING

<160> NUMBER OF SEQ ID NOS: 3

<210> SEQ ID NO 1
<211> LENGTH: 458
<212> TYPE: PRT
<213> ORGANISM: Sinorhizobium arboris

<400> SEQUENCE: 1

```
Met Asn Ile Ala Ala Gln Ser Trp Glu Arg Arg Glu Ala Thr Ser Phe
1               5                   10                  15

Phe His Thr Phe Thr Asp Leu Pro Ser Leu Lys Thr Asp Gly Pro Val
            20                  25                  30

Ile Ile Asp His Gly Glu Gly Pro Tyr Ile Ile Asp Thr Val Gly Arg
        35                  40                  45

Arg Tyr Phe Glu Gly Asn Ser Gly Leu Trp Asn Met Thr Leu Gly Phe
    50                  55                  60

Ser Glu Arg Arg Leu Ser Asp Ala Ala Leu Lys Gln Tyr Gln Glu Phe
65                  70                  75                  80

Pro Gly Tyr His Thr Phe Phe Gly Arg Asn Ser Lys Pro Thr Val Glu
                85                  90                  95

Leu Ala Glu Arg Met Leu Lys Leu Ala Pro Ala Pro Met Ser Arg Val
            100                 105                 110

Phe Phe Thr Asn Ser Gly Ser Glu Ala Asn Glu Ser Ile Val Lys Leu
        115                 120                 125

Leu Trp Met Met Trp Ala Ala Glu Gly Arg Pro Glu Arg Arg Lys Leu
    130                 135                 140

Leu Thr Arg Lys Asn Ala Tyr His Gly Ala Thr Val Met Ala Ser Ala
145                 150                 155                 160

Leu Thr Gly Lys Asp Tyr Val Lys Ala Phe Gly Leu Pro Gly Pro Glu
                165                 170                 175

Ile Val Thr Leu Asp Cys Pro His Ala Trp Arg Phe Ala Leu Pro Gly
            180                 185                 190

Glu Gly Asp Asp Glu Phe Ala Ala Arg Leu Ala Ala Asn Leu Glu Thr
        195                 200                 205

Arg Ile Leu Gln Glu Gly Pro Glu Thr Ile Ala Gly Met Phe Ala Glu
    210                 215                 220
```

```
Pro Val Met Gly Ala Gly Val Ile Val Pro Ala Thr Tyr Phe
225                 230                 235                 240

Ala Lys Ile Gln Pro Val Leu Gln Arg Tyr Gly Ile Pro Leu Ile Ala
                245                 250                 255

Asp Glu Val Ile Cys Gly Phe Gly Arg Thr Gly Ser Leu Trp Gly Thr
                260                 265                 270

Leu Ala Val Gly Gln Gln Pro Asp Ile Ile Val Ala Ser Lys Ser Met
                275                 280                 285

Ser Ala Gly Tyr Phe Pro Met Gly Ala Val Met Leu Ser Ala Asp Ile
                290                 295                 300

Asp Lys Arg Ala Thr Ala Ala Ser Glu Val Trp Glu Glu Phe Pro His
305                 310                 315                 320

Gly Phe Thr Thr Gly Gly His Pro Val Gly Cys Ala Ile Ser Leu Glu
                325                 330                 335

Ala Ile Arg Ile Ile Thr Glu Glu Gly Val Phe Glu Asn Val Lys Ser
                340                 345                 350

Val Ser Glu Thr Phe Gln Ser Gly Leu Arg Ala Leu Ala Asp His Pro
                355                 360                 365

Met Ile Gly Glu Ala Arg Gly Met Gly Leu Met Gly Ala Leu Glu Thr
370                 375                 380

Val Ala Asp Lys Lys Thr Lys Gln Ser Phe Ser Gly Asp Leu Arg Ile
385                 390                 395                 400

Gly Glu Arg Ile Ser Lys Glu Ala Arg Asp Arg Gly Phe Ile Ile Arg
                405                 410                 415

Pro Leu Gly Ser Ser Val Val Leu Ala Pro Pro Phe Ile Ser Thr His
                420                 425                 430

Gly Gln Ile Glu Glu Leu Leu Ala Val Leu Lys Glu Val Leu Asp Val
                435                 440                 445

Val Tyr Gly Thr Val Lys Gly Glu Val Ala
                450                 455

<210> SEQ ID NO 2
<211> LENGTH: 368
<212> TYPE: PRT
<213> ORGANISM: Rhodosporidium toruloides

<400> SEQUENCE: 2

Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Asn Trp Thr Pro Phe Met Thr Leu Thr Asp Gly
        50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
                100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
        130                 135                 140
```

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
            165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Met Asp Ser Ser Asp Pro Ala Ser Pro Ala Tyr Ile
            210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
                260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 3
<211> LENGTH: 426
<212> TYPE: PRT
<213> ORGANISM: Escherichia coli

<400> SEQUENCE: 3

Met Asn Ser Asn Lys Glu Leu Met Gln Arg Ser Gln Ala Ile Pro
1               5                   10                  15

Arg Gly Val Gly Gln Ile His Pro Ile Phe Ala Asp Arg Ala Glu Asn
                20                  25                  30

Cys Arg Val Trp Asp Val Glu Gly Arg Glu Tyr Leu Asp Phe Ala Gly
            35                  40                  45

Gly Ile Ala Val Leu Asn Thr Gly His Leu His Pro Lys Val Val Ala
    50                  55                  60

Ala Val Glu Ala Gln Leu Lys Lys Leu Ser His Thr Cys Phe Gln Val
65                  70                  75                  80

Leu Ala Tyr Glu Pro Tyr Leu Glu Leu Cys Glu Ile Met Asn Gln Lys
                85                  90                  95

Val Pro Gly Asp Phe Ala Lys Lys Thr Leu Leu Val Thr Thr Gly Ser
            100                 105                 110

Glu Ala Val Glu Asn Ala Val Lys Ile Ala Arg Ala Thr Lys Arg
            115                 120                 125

Ser Gly Thr Ile Ala Phe Ser Gly Ala Tyr His Gly Arg Thr His Tyr
            130                 135                 140

Thr Leu Ala Leu Thr Gly Lys Val Asn Pro Tyr Ser Ala Gly Met Gly

-continued

```
145                 150                 155                 160
Leu Met Pro Gly His Val Tyr Arg Ala Leu Tyr Pro Cys Pro Leu His
                165                 170                 175

Gly Ile Ser Glu Asp Asp Ala Ile Ala Ser Ile His Arg Ile Phe Lys
                180                 185                 190

Asn Asp Ala Ala Pro Glu Asp Ile Ala Ile Val Ile Glu Pro Val
                195                 200                 205

Gln Gly Glu Gly Gly Phe Tyr Ala Ser Ser Pro Ala Phe Met Gln Arg
    210                 215                 220

Leu Arg Ala Leu Cys Asp Glu His Gly Ile Met Leu Ile Ala Asp Glu
225                 230                 235                 240

Val Gln Ser Gly Ala Gly Arg Thr Gly Thr Leu Phe Ala Met Glu Gln
                245                 250                 255

Met Gly Val Ala Pro Asp Leu Thr Thr Phe Ala Lys Ser Ile Ala Gly
                260                 265                 270

Gly Phe Pro Leu Ala Gly Val Thr Gly Arg Ala Glu Val Met Asp Ala
                275                 280                 285

Val Ala Pro Gly Gly Leu Gly Gly Thr Tyr Ala Gly Asn Pro Ile Ala
                290                 295                 300

Cys Val Ala Ala Leu Glu Val Leu Lys Val Phe Glu Gln Glu Asn Leu
305                 310                 315                 320

Leu Gln Lys Ala Asn Asp Leu Gly Gln Lys Leu Lys Asp Gly Leu Leu
                325                 330                 335

Ala Ile Ala Glu Lys His Pro Glu Ile Gly Asp Val Arg Gly Leu Gly
                340                 345                 350

Ala Met Ile Ala Ile Glu Leu Phe Glu Asp Gly Asp His Asn Lys Pro
                355                 360                 365

Asp Ala Lys Leu Thr Ala Glu Ile Val Ala Arg Ala Asp Lys Gly
                370                 375                 380

Leu Ile Leu Leu Ser Cys Gly Pro Tyr Tyr Asn Val Leu Arg Ile Leu
385                 390                 395                 400

Val Pro Leu Thr Ile Glu Asp Ala Gln Ile Arg Gln Gly Leu Glu Ile
                405                 410                 415

Ile Ser Gln Cys Phe Asp Glu Ala Lys Gln
                420                 425
```

METHODS FOR MAKING L-GLUFOSINATE

CROSS-REFERENCE TO PRIORITY APPLICATIONS

This application is a continuation of U.S. application Ser. No. 16/287,290, filed Feb. 27, 2019, now U.S. Pat. No. 10,781,465, which is a continuation of U.S. application Ser. No. 15/787,448, filed Oct. 18, 2017, now U.S. Pat. No. 10,260,078, which is a division of U.S. application Ser. No. 15/445,254, filed Feb. 28, 2017, now U.S. Pat. No. 9,834,802, which claims priority to U.S. Provisional Application No. 62/302,421, filed Mar. 2, 2016; U.S. Provisional Application No. 62/336,989, filed May 16, 2016; and U.S. Provisional Application No. 62/413,240, filed Oct. 26, 2016. These applications are incorporated herein by reference in their entireties.

Described herein are methods for producing a single stereoisomer of glufosinate, particularly for the production of L-glufosinate.

BACKGROUND

The herbicide glufosinate is a non-selective, foliarly-applied herbicide considered to be one of the safest herbicides from a toxicological or environmental standpoint. Current commercial chemical synthesis methods for glufosinate yield a racemic mixture of L- and D-glufosinate (Duke et al. 2010 Toxins 2:1943-1962). However, L-glufosinate (also known as phosphinothricin or (S)-2-amino-4-(hydroxy(methyl)phosphonoyl)butanoic acid) is much more potent than D-glufosinate (Ruhland et al. (2002) Environ. Biosafety Res. 1:29-37).

Therefore, methods are needed to produce only or primarily the active, L-glufosinate form. Previously, cost effective methods to generate pure L-glufosinate, or a mixture of D- and L-glufosinate enriched for L-glufosinate, have not been available. Described herein are new and cost-effective methods for the production of L-glufosinate.

SUMMARY

Compositions and methods for making L-glufosinate are provided. The first step of the process involves the oxidative deamination of D-glufosinate to PPO (2-oxo-4-(hydroxy(methyl)phosphinoyl)butyric acid). The second step involves the specific amination of PPO to L-glufosinate, using an amine group from one or more amine donors. In some embodiments, the method involves reacting D-glufosinate with a D-amino acid oxidase (DAAO) enzyme to form PPO (2-oxo-4-(hydroxy(methyl)phosphinoyl)butyric acid); followed by aminating the PPO to L-glufosinate by a transaminase (TA) enzyme, using an amine group from one or more amine donors, wherein at least 70% of the D-glufosinate is eliminated and/or the yield of L-glufosinate is at least 85% of the input racemic glufosinate or at least 70 to 85% of the D-glufosinate is converted to L-glufosinate. In some embodiments, unreacted amine donor from one reaction can be reused in further rounds of reaction. Optionally, the D-glufosinate is originally present (i.e., in the reacting step) in a racemic mixture of D- and L-glufosinate.

The DAAO enzyme must have an increased activity of about 3 umol/min*mg or greater to drive the reaction. DAAO enzymes are available in the art and can be modified or mutated to have the necessary increased activity needed to drive the process. In this manner, mutant or modified enzymes from *Rhodosporidium toruloides* (UniProt P80324), *Trigonopsis variabilis* (UniProt Q99042), *Neolentinus lepideus* (GenBank KZT28066.1), *Trichoderma reesei* (GenBank XP_006968548.1), or *Trichosporon oleaginosus* (KLT40252.1) can be used. In some embodiments, the DAAO enzyme is a mutant DAAO based on the sequence from *Rhodosporidium toruloides*. While a number of mutations can be made and tested for the effect on activity, the mutant DAAO in some embodiments may comprise mutations at positions 54, 56, 58, 213, and/or 238. For example, the mutant DAAO can comprise one or more of the following mutations at position 54: N54C, N54L, N54T, or N54V. The mutant DAAO can optionally comprise the following mutation at position 56: T56M. The mutant DAAO can optionally comprise one or more of the following mutations at position 58: F58A, F58G, F58H, F58K, F58N, F58Q, F58R, F58S, or F58T. Optionally, the mutant DAAO can comprise the following mutation at position 213: M213S. In some embodiments, the mutant DAAO can comprise one or more of the following combinations of mutations: F58K and M213S; N54T and T56M; N54V and F58Q; and/or N54V, F58Q, and M213S. In each case, the enzyme needs to have an activity of equal to or greater than about 3 umol/min*mg, greater than about 4 umol/min*mg, or higher. A wild type enzyme can be used in the methods of the invention as long as the enzyme has an activity level as set forth above.

The TA enzyme may be a gabT transaminase from *Escherichia coli* (UniProt P22256). Alternatively, the TA enzyme may be a transaminase with the sequence identified as SEQ ID NO: 1. The TA enzyme may also be selected on the basis of sequence similarity to SEQ ID NO: 1 and/or mutated to improve its activity in the desired reaction. Thus, sequences having 80%, 85%, 90%, 95% or greater sequence identity to SEQ ID NO: 1, based on the BLASTP method of alignment, and retain transaminase activity are encompassed by the present invention. Any DNA sequence encoding the enzyme sequence of SEQ ID NO: 1 or variants thereof are encompassed herein as well.

The reacting step and the aminating step can be performed in a single container or in separate containers. In one embodiment, all reagents are substantially added at the start of the reaction. Alternatively, the reagents for the reacting step and the reagents for the aminating step are added to the single container at different times.

Also described herein is a method for selectively controlling weeds in a field containing a crop of planted seeds or crops that may optionally be resistant to glufosinate, comprising applying an effective amount of a composition comprising L-glufosinate at an enantiomeric excess of greater than 90% over D-glufosinate to the field. Also described herein is a method for selectively controlling weeds in a field, controlling weeds in non-field areas, defoliating plants or crops, and/or desiccating crops before harvest, comprising applying an effective amount of a composition comprising L-glufosinate at an enantiomeric excess of greater than 90% over D-glufosinate and more than 0.01% but less than 15% PPO to the field.

The details of one or more embodiments are set forth in the drawings and the description below. Other features, objects, and advantages will be apparent from the description and drawings, and from the claims.

Some compositions of the invention comprise D-glufosinate, PPO, and L-glufosinate. In such compositions, L-glufosinate is present at a concentration equal to or greater than 80%, greater than 90%, greater than 95%, greater than 96%, greater than 97%, greater than 98%, or greater than 99% by weight of the composition, based on the combined weight of D-glufosinate, PPO, and L-glufosinate. Other compositions comprise L-glufosinate at concentrations equal to 80% or greater after isolation of the L-glufosinate from the present reaction mixture.

DETAILED DESCRIPTION

Figure 2:
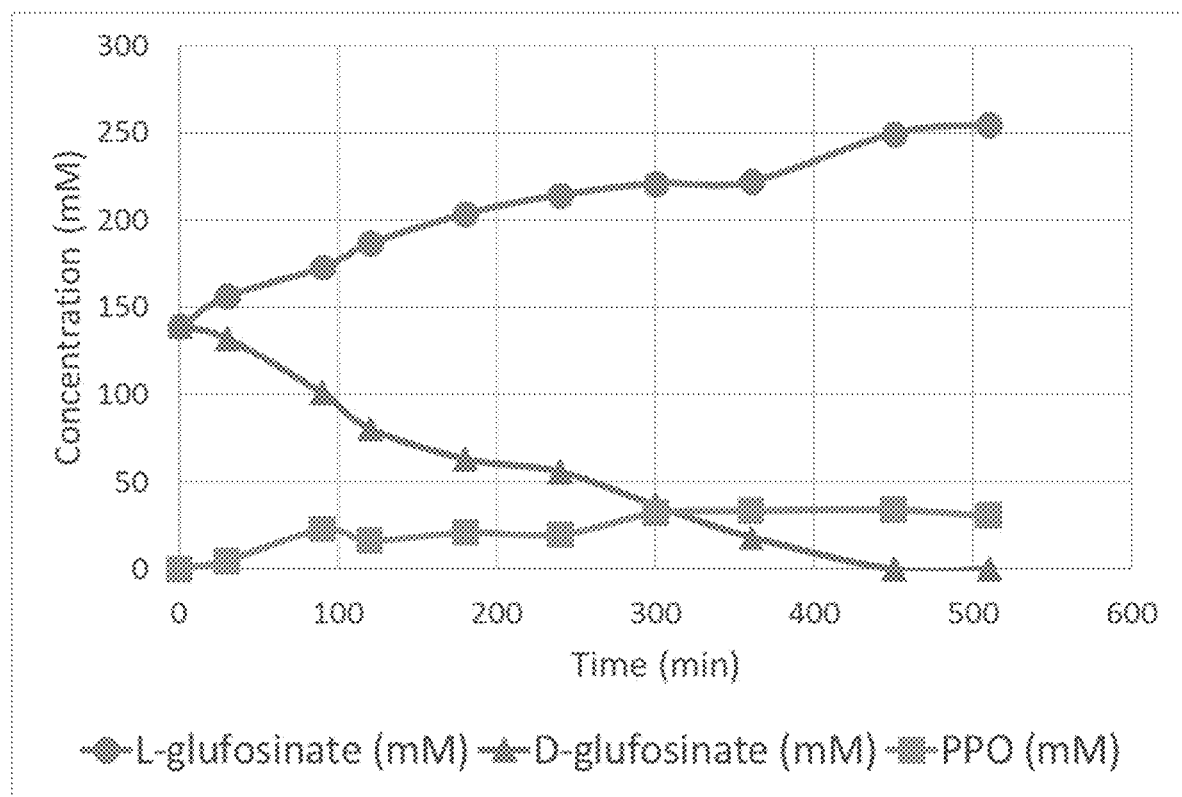
FIG. 2 is a graph showing concentrations of L-glufosinate (circles), D-glufosinate (triangles), and PPO (squares) during a one-step de-racemization by a N54T, T56M, F58K, and M213S mutant variant of *Rhodosporidium toruloides* DAAO and the *E. coli* gabT transaminase.

Compositions and methods for the production of L-glufosinate (also known as phosphinothricin or (S)-2-amino-4-(hydroxy(methyl)phosphonoyl)butanoic acid) are provided. The methods comprise a two-step process, which may optionally occur in a single vessel and nearly simultaneously. The first step involves the oxidative deamination of D-glufosinate to PPO (2-oxo-4-(hydroxy(methyl)phosphinoyl)butyric acid). The second step involves the specific amination of PPO to L-glufosinate, using an amine group from one or more amine donors. By combining these two reactions, the proportion of L-glufosinate can be substantially increased in a racemic glufosinate mixture. Thus, provided herein are methods to obtain a composition consisting substantially of L-glufosinate. Since L-glufosinate is more potent than D-glufosinate, smaller amounts of the composition are needed to be effective as a herbicide.

In one embodiment, described herein, is a composition comprising a mixture of L-glufosinate, PPO, and D-glufosinate, where L-glufosinate is the predominant compound among the mixture of L-glufosinate, PPO, and D-glufosinate. Such composition can be used directly as a herbicide as PPO can contribute herbicidal activity (EP0030424). In other embodiments, L-glufosinate can be purified or substantially purified and used as a herbicide.

Compositions of L-glufosinate may comprise D-glufosinate, PPO, and L-glufosinate. Optionally, the amount of L-glufosinate is 80% or greater, 85% or greater, 90% or greater, or about 95% or greater, 97% or greater, 98% or greater based on the combined weight of D-glufosinate, PPO, and L-glufosinate. Optionally, the amount of D-glufosinate is 10% or less, 5% or less, 2.5% or less, or 1% or less based on the combined weight of D-glufosinate, PPO, and L-glufosinate. Optionally, the amount of PPO is more than 1% but less than 20%, less than 15%, less than 10%, or less than 5% based on the weight of D-glufosinate, PPO, and L-glufosinate. These compositions can optionally occur as dried powders or dissolved in aqueous or non-aqueous carrier and additional chemical species can optionally be present. Optionally, the composition is prepared and used in an ex vivo environment.

It is also recognized that the L-glufosinate can be further isolated and used in formulations as a herbicide.

Also described herein are formulations. The formulations comprise L-glufosinate ammonium in an amount from 10-30% by weight of the formulation; one or more additional components selected from the group consisting of sodium alkyl ether sulfate in an amount from 10-40% by weight of the formulation; 1-methoxy-2-propanol in an amount from 0.5-2% by weight of the formulation; dipropylene glycol in an amount from 4-18% by weight of the formulation; and alkyl polysaccharide in an amount from 4-20% by weight of the formulation; and water as the balance of the formulation. Optionally, the formulation comprises L-glufosinate ammonium in an amount of 12.25% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 36.75% by weight of the formulation. Optionally, the formulation comprises L-glufosinate ammonium in an amount of 24.5% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 24.5% by weight of the formulation. Optionally, the formulation comprises L-glufosinate ammonium in an amount of 12.25% by weight of the formulation; sodium alkyl ether sulfate in an amount of 15.8% by weight of the formulation; 1-methoxy-2-propanol in an amount of 0.5% by weight of the formulation; dipropylene glycol in an amount of 4.3% by weight of the formulation; alkyl polysaccharide in an amount of 4.9% by weight of the formulation; and water in an amount of 62.25% by weight of the formulation. Optionally, the formulation comprises L-glufosinate ammonium in an amount of 24.5% by weight of the formulation; alkylethersulfate, sodium salt in an amount of 22.1% by weight of the formulation; 1-methoxy-2-propanol in an amount of 1.0% by weight of the formulation; alkyl polysaccharide in an amount of 6.2% by weight of the formulation; and water in an amount of 46.2% by weight of the formulation.

While the methods can be used to produce a substantially purified L-glufosinate in a batch reaction, it is recognized that a continuous process can be used.

I. Methods of Synthesis

Methods for the conversion of D-glufosinate to L-glufosinate are provided. The methods described herein provide a means for converting a low cost feedstock of a racemic mixture of D- and L-glufosinate into a more valuable product that has been enriched for L-glufosinate. The methods for conversion includes two steps, which can occur in one or more separate containers. The first step is the oxidative deamination of D-glufosinate (which can be present in a racemic mixture of D- and L-glufosinate) to PPO (2-oxo-4-(hydroxy(methyl)phosphinoyl)butyric acid). This step can be catalyzed by a D-amino acid oxidase (DAAO) enzyme, a D-amino acid dehydrogenase (DAAD) enzyme, or by chemical conversion. The second step is the specific amination of PPO to L-glufosinate, using an amine group from one or more amine donors. Such amine donors can be selected from glutamate, L-glutamate, lysine, alanine, isopropylamine, sec-butylamine, phenylethylamine and the like. This step can be catalyzed by a transaminase (TA) enzyme, an L-amino acid dehydrogenase (LAAD) enzyme, or by chemical conversion. Using the methods described herein, compositions of substantially purified L-glufosinate can be obtained.

Figure 1:
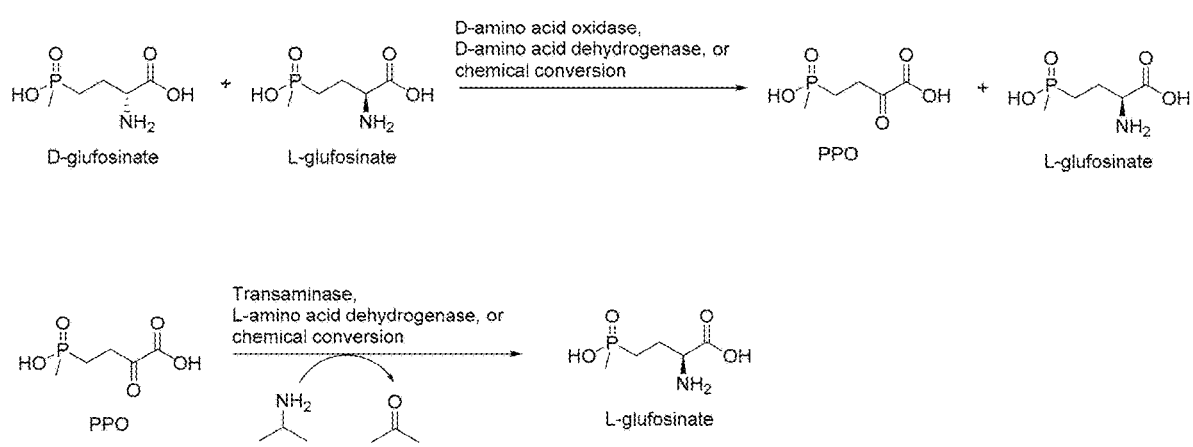
FIG. 1 is a schematic of an exemplary conversion of D-glufosinate to L-glufosinate. The amine donor and keto acid product are examples and are not intended to be limiting.

FIG. 1 sets forth an example of the conversion of D-glufosinate to L-glufosinate. As noted above, the method involves a two-step process. As illustrated, the first step is an oxidative deamination of D-glufosinate to PPO and the second step is an amination of PPO to L-glufosinate.

The first step, i.e., the oxidative deamination of D-glufosinate to PPO, can be catalyzed by several classes of enzymes or can occur non-enzymatically. Such enzymes include DAAO, DAAD, and D-amino acid dehydratase.

In one embodiment a DAAO enzyme is used to catalyze the conversion of D-glufosinate to PPO. Such a reaction has the following stoichiometry:

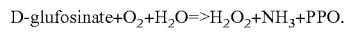

D-glufosinate+$O_2$+$H_2O$=>$H_2O_2$+$NH_3$+PPO.

Since the solubility of oxygen in aqueous reaction buffer is typically low compared to that of glufosinate, for an efficient process, oxygen must be introduced throughout the time period of the DAAO reaction. This is in contrast to, for example, the Hawkes reaction set forth in U.S. Pat. Nos. 7,723,576; 7,939,709; 8,642,836; and 8,946,507 in which the reaction was conducted in a sealed vessel. Initially, D-glufosinate is present at greater than 30 g/L up to as much as 140 g/L. The initial oxygen level is typically impacted by the reaction temperature, but is typically initially present at approximately 8 mg/L and is added throughout the reaction to allow for sufficient oxygen for the reaction to continue apace. Water is typically, but not obligately, present at greater than 500 g/L.

Several DAAO enzymes are known in the art and can be used in the methods described herein, as long as they are capable of accepting D-glufosinate as a substrate and provide an activity sufficient to level to drive the reaction. The DAAO enzymes useful in the methods of the invention have an activity of equal to or greater than about 3 umol/min*mg, greater than about 4 umol/min*mg, or higher. A wild type enzyme can be used in the methods of the invention as long as the enzyme has an activity level as set forth above. Such DAAO enzymes that can be used in the method include those from *Rhodosporidium toruloides, Trigonopsis variabilis, Fusarium* sp, *Candida* sp, *Schizosasaccharomyces* sp, *Verticillium* sp, *Neolentinus lepideus, Trichoderma reesei, Trichosporon oleaginosus*, and the like that have been modified to increase activity. Any DAAO enzyme can be used as a starting enzyme including those having sequences corresponding to Swissprot accession numbers P80324, Q99042, P00371, and P24552 or SPTREMBL numbers Q9HGY3 and Q9Y7N4 or GenBank numbers KZT28066.1, XP_006968548.1, and KLT40252.1. The DNA sequences which encode the DAAO may be selected from sequences set forth in EMBL accessions A56901, RGU60066, Z50019, SSDA04, D00809, AB042032, RCDAAOX, A81420, and SPCC1450, or may be codon optimized from the protein sequences indicated above for optimal expression in the chosen expression host(s). U.S. Pat. No. 8,227,228 describes DAAO enzymes from *Candida intermedia*. Such sequences are herein incorporated by reference. These enzymes can be modified for increased activity and used in the methods of the invention.

Additional DAAO enzymes can be identified in a variety of ways, including sequence similarity and functional screens. The DAAO enzyme may be a mutant DAAO enzyme that is capable of accepting D-glufosinate as a substrate. In Hawkes et al., supra, a mutant DAAO based on the sequence from *Rhodosporidium toruloides* (consisting of the F58K and M213S mutations) has been shown to accept D-glufosinate as a substrate (Hawkes et al. (2011) *Plant Biotechnol.* 9(3):301-14). Other DAAO enzymes can be similarly modified to accept D-glufosinate and have greater activity. i.e., the activity needed to drive the method of the invention. In the same manner, known DAAO enzymes may be improved by mutagenesis, and/or novel DAAO enzymes could be identified.

In some embodiments, mutant enzymes can be made and tested in the methods described herein. Mutant DAAO enzymes (e.g., from *Rhodotorula gracilis*) can include one mutation, two mutations, three mutations, or more than three mutations (e.g., four mutations, five mutations, six mutations, seven mutations, eight mutations, nine mutations, or ten mutations or more) at positions in the mutant sequence as compared to the wild type sequence. The mutant DAAO can optionally comprise mutations at positions 54, 56, 58, 213, and/or 238. In some embodiments, such mutants can comprise amino acid substitutions at positions 54 and 56 when compared with the wild type sequence. In other embodiments, such mutants can comprise amino acid substitutions at positions 54 and 58 when compared to the wild type sequence. In other embodiments, such mutants can include amino acid substitutions at positions 54, 213, and 238 when compared with the wild type sequence.

Optionally, at position 54, the wild type asparagine may be replaced by Ala, Cys, Gly, Ile, Ser, Leu, or, more preferably, Thr or Val. For example, the mutant DAAO can comprise one of the following mutations at position 54: N54C, N54L, N54T, or N54V.

Optionally, at position 56, the wild type threonine can be replaced by Ala, Cys, Gly, Ile, Asn, Arg, Ser, Thr, Met, or Val. See, U.S. Pat. No. 7,939,709, which is incorporated herein by reference. For example, the mutant DAAO can comprise the T56M mutation.

Additionally, at position 58, the wild type Phe can be replaced by Lys, Arg, Gln, Thr, Gly, Ser, Ala, Arg, Asn, or His. The mutant DAAO can optionally comprise one of the following mutations at position 58: F58A, F58G, F58H, F58K, F58N, F58Q, F58R, F58S, or F58T. In some embodiments, the mutant DAAO does not include a mutation at position 58.

Optionally, at position 213, the wild type methionine is replaced by Arg, Lys, Ser, Cys, Asn, or Ala. In some examples, the mutant DAAO can comprise the mutation M213S.

Optionally, at position 238, the wild type tyrosine is replaced by His, Ser, Gys, Asn, or Ala.

In some embodiments, the mutant DAAO can comprise one or more of the following combinations of mutations: F58K and M213S; N54T and T56M; N54V and F58Q; N54C and F58H; N54T and F58T; N54T and F58G; N54T and F58Q; N54T and F58A; N54L and F58R; N54V and F58R; N54V and F58N; and/or N54V, F58Q, and M213S.

In one embodiment, the mutant DAAO comprises mutations in other DAAO enzymes in positions equivalent to positions 54, 56, 58, 213, and/or 238 of *Rhodosporidium toruloides* DAAO or *Trigonopsis variabilis* DAAO.

Other suitable D amino acid oxidases may be obtained preferably from fungal sources. Such DAAO enzymes can be identified and tested for use in the methods of the invention. To determine if the enzyme will accept D-glufosinate as a substrate, an oxygen electrode assay (Hawkes, 2011, supra), colorimetric assay (Berneman A, Alves-Ferreira M, Coatnoan N, Chamond N, Minoprio P (2010) Medium/High Throughput D-Amino Acid Oxidase Colorimetric Method for Determination of D-Amino Acids. Application for Amino Acid Racemases. *J Microbial Biochem Technol* 2: 139-146), and/or direct measurement (via high performance liquid chromatography (HPLC), liquid chromatography mass spectrometry (LC-MS), or similar) of product formation can be employed.

The reaction catalyzed by the DAAO enzyme requires oxygen. In some embodiments, oxygen, oxygen enriched air, an oxygen enriched gas stream, or air, is introduced to the reaction, either in the head space or by sparging gas through the reaction vessel, intermittently or continuously, to enhance the rate of reaction. Additionally, in other embodiments, optionally combined with sparging gas through the reaction vessel, a pressurized reactor may be used. That is, the reactor may be sealed and allowed to consume 02. Using a sealed chamber would limit vapor emissions.

When a DAAO enzyme catalyzes the conversion of D-glufosinate to PPO, hydrogen peroxide ($H_2O_2$) evolves. This may be damaging to enzymes and other components of the biotransformation (e.g., products and/or substrates). Therefore, in one embodiment, an enzyme, such as catalase, can be used in addition to the DAAO enzyme to catalyze the elimination of hydrogen peroxide. Catalase catalyzes the decomposition of hydrogen peroxide with the following stoichiometry:

$$2H_2O_2 => 2H_2O + O_2.$$

In some embodiments, hydrogen peroxide can be eliminated using catalyzed and non-catalyzed decomposition reactions. For example, hydrogen peroxide can be eliminated by a non-catalyzed decomposition reaction using increased heat and/or pH. Hydrogen peroxide can also be eliminated by a catalyzed decomposition reaction using, for example, transition metals and other agents, such as potassium iodide. In addition to eliminating hydrogen peroxide, the use of catalase also produces oxygen ($O_2$). The production of oxygen by catalase can aid in facilitating the conversion of D-glufosinate to PPO using the DAAO enzyme, as DAAO requires oxygen to function.

Other enzymes can be used to catalyze the conversion of D-glufosinate to PPO. For example, a DAAD enzyme that accepts D-glufosinate as a substrate can be used with the following stoichiometry:

D-glufosinate+$H_2O$+acceptor=>$NH_3$+reduced acceptor+PPO.

It is recognized that in methods where a DAAD is used, the DAAD catalyzed reaction can include redox cofactor recycling. This involves oxidizing the reduced acceptor so that it can accept more electrons from D-glufosinate.

In one embodiment, chemical oxidative deamination, wherein an intermediate α-keto acid is produced from the parent amino acid, can be used in the methods described herein to convert D-glufosinate to L-glufosinate. Chemical oxidative deamination involves the conversion of an amine group to a keto group with concomitant release of ammonia typically using metal ions such as those of copper or cobalt in an aqueous solution at temperatures between room temperature and the boiling point of the solution and at a pH in the range of about 4-about 10. See, for example, Ikawa and Snell (1954) *J. Am. Chem. Soc.* 76 (19): 4900-4902, herein incorporated by reference.

The substantially complete (greater than 70%, greater than 75%, greater than 80%, greater than 85%, greater than 90%, or greater than 95%) conversion of D-glufosinate to PPO can occur within 24 hours, within 18 hours, within 12 hours, within 8 hours or less.

The second step of the method described herein involves the conversion of PPO to L-glufosinate using a transaminase (TA) enzyme, an L-amino acid dehydrogenase (LAAD) enzyme, or by chemical conversion. In one embodiment, the method is a reaction catalyzed by a TA. A TA with the required stereospecificity that accepts PPO as a substrate catalyzes the amination of PPO to L-glufosinate with the following stoichiometry:

PPO+amine donor=>L-glufosinate+keto acid.

If the reaction is conducted as a two stage process where the D-glufosinate is substantially converted to PPO in the absence of amine donor and/or transaminase, starting amounts of PPO in the second stage typically range from 10 g/L to 140 g/L; 20 g/L to 140 g/L; or from 30 g/L to 140 g/L. If the reaction is conducted in a single stage process, the starting amounts of PPO are typically less than 1 g/L and the highest levels of PPO during the reaction are typically less than 25 g/L. The amine donor is initially present at between 1 and 50 fold molar excess over the starting amount of racemic glufosinate.

TAs useful in the methods described herein include the gabT transaminase from *Escherichia coli* (UniProt P22256; identified herein as SEQ ID NO: 3), which has been shown to catalyze the desired reaction with PPO as a substrate (Bartsch et al. (1990) *Appl Environ Microbiol.* 56(1):7-12). Another enzyme has been evolved to catalyze the desired reaction at a higher rate using isopropylamine as an amine donor (Bhatia et al. (2004) Peptide Revolution: Genomics, Proteomics & Therapeutics, Proceedings of the Eighteenth American Peptide Symposium, Ed. Michael Chorev and Tomi K. Sawyer, Jul. 19-23, 2003, pp. 47-48). A transaminase with the amino acid sequence of SEQ ID NO: 1 also catalyzes the desired reaction with PPO and isopropylamine as the substrate (Example 11). Additionally, TA enzymes from numerous microorganisms, such as *Streptomyces hygroscopicus, Streptomyces viridochromogenes, Candida albicans*, and others can be used in the practice of the methods described herein. In particular, see, for example, EP0249188, and U.S. Pat. No. 5,162,212, incorporated herein by reference. Where desired, the enzymes can be evolved by mutagenesis to increase their activities. Mutant TA enzymes can be selected for desired activity by the assays outlined in Schulz et al., Appl Environ Microbiol. (1990) January 56(1):1-6, and/or by direct measurement of the products by HPLC, LC-MS, or similar products.

Additional TA enzymes for use in the methods can be identified by screening collections of TAs, such as those sold by Prozomix Limited (Northumberland, United Kingdom), SyncoZymes (Shanghai, China), Evocatal (Monheim am Rhein, Germany), Codexis (Redwood City, Calif.), or Abcam (Cambridge, United Kingdom) for the desired activity. Alternatively, sequence similarity can be used to identify novel TA enzymes. Finally, TA enzymes can also be identified from organisms capable of catalyzing the desired reaction.

The selection of an appropriate amine donor is important for an economical conversion of D-glufosinate to L-glufosinate. A variety of issues may be considered, including the cost of the donor, equilibrium thermodynamics, potential recovery of the donor, separation of the keto acid product from the desired L-glufosinate, and others. Consequently, TA enzymes that accept several different amine donors can be used, including low cost amine donors such as L-aspartate or racemic aspartate, L-glutamate or racemic glutamate, L-alanine or racemic alanine, L-phenylethylamine or racemic phenylalanine, L-glycine or racemic glycine, L-lysine or racemic lysine, L-valine or racemic valine, L-serine or racemic serine, L-glutamine or racemic glutamine, isopropylamine, sec-butylamine, ethanolamine, 2-aminobutyric acid, and diaminoproprionic acid. In some embodiments, the amine donor is not aspartate or aspartic acid (e.g., L-aspartic acid, D-aspartic acid, or racemic D,L-aspartic acid).

In embodiments where the amino donor is glutamate, the keto acid co-product that results from the transamination reaction is α-ketoglutarate (which is also referred to as α-ketoglutaric acid or α-KG). The α-ketoglutarate can be isolated and/or purified using methods known to those of skill in art, such as in EP Patent No. 0073711, CN Patent No. 10519873, CN Patent No. 105177065, CN Patent No. 104529755, and Zhan et al., *Shipin Yu Shengwu Jishu Xuebao*, 32(10): 1043-1048 (2013), each of which are incorporated herein by reference in their entireties. The produced and isolated α-ketoglutarate can be used in a variety of applications, including in synthesizing pharmaceutical agents, food additives, and biomaterials. Optionally, the α-ketoglutarate can be chemically converted to either racemic glutamate or L-glutamate, optionally for reuse in the reaction.

Chemical reductive amination involves the conversion of a keto group to an amine group via an imine compound typically by treatment of the keto compound with a suitable amine in an organic solution. Suitable amines include, for example, methylamine or ammonia. Suitable organic solvents for use in the organic solution include tetrahydrofuran, ethanol, or dichloromethane (DCM). The reductive amination can be performed at temperatures between room temperature and the boiling point of the solution. The produced imine can then be reduced using a reducing agent in an organic solution. Suitable reducing agents include, for example, $NaBH_4$, $NaHB(OAc)_3$, or $Na(CN)BH_3$. Suitable organic solvents for use in the organic solution include tetrahydrofuran, ethanol, or DCM. The reduction reaction can be performed at temperatures between 0° C. and the boiling point of the solution. Those skilled in the art will know that the process may be done in "one-pot" or in multiple containers, i.e., in separate transformations. Additionally, those skilled in the art will recognize that the described procedure will provide racemic amino material where possible. The use of a chiral reducing agent such as $RuCl_2[(S)\text{-BINAP}]$ and hydrogen gas or latent source of hydrogen gas, or achiral hydride based reducing agents in the presence chiral ligands such as (S)- or (R)-VAPOL in a ratio between 1:1 to 1:0.05 can produce enantiomerically pure and/or enriched amino material. See, for example, Mignonac (1921) *Compt. Rend.* 172:223 and G. Li, Y. Liang, J. C. Antilla (2007) *J. Am. Chem. Soc.*, 129:5830-5831.

A wild type TA that accepts a desired amine donor can be identified, or a TA that does not normally accept a desired amine donor can be evolved to accept the desired substrate. Optionally, the transaminase is not an aspartate transaminase. Optionally, the transaminase is not 4-amino-butyrate:2-ketoglutarate transaminase. In some embodiments, the transaminase is not a combination enzyme system that includes a PPT-specific transaminase and glutamate:oxaloacetate transaminase.

Other enzymes for use to catalyze the conversion of PPO to L-glufosinate include LAAD enzymes or imine reductases that accept PPO as a substrate. Such LAAD enzymes use the following stoichiometry:

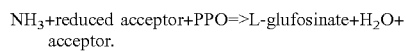

LAAD catalyzed reactions can include redox cofactor recycling, which involves reducing the oxidized acceptor so that it can donate more electrons to PPO.

Chemical reductive amination, wherein an amino group is produced from the parent keto-compound, can also be used to produce glufosinate, in the case where no chiral reductant or ligand is used, or L-glufosinate, in the case where a chiral reductant or ligand is used. Chemical reductive amination can be affected as described above.

The substantially complete conversion of PPO to L-glufosinate may occur within 24 hours, within 18 hours, within 12 hours, within 8 hours, or within 4 hours. Substantially complete, in this context, means that the conversion of PPO to L-glufosinate is greater than about 70%, greater than about 75%, greater than about 80%, greater than about 85%, greater than about 90%, greater than about 95%, greater than about 98%, or greater than about 99%.

If the reaction occurs in a single container or vessel, the TA enzyme can be added with the DAAO enzyme or added at a later time, e.g., after the DAAO enzyme has been allowed to catalyze some or substantially all of the oxidative deamination.

Enzymes can be added to the reaction by a number of methods. One approach is to express the enzyme(s) in microorganism(s) such as *E. coli*, *S. cerevisiae*, *P. pastoris*, and others, and to add the whole cells to the reactions as whole cell biocatalysts. Another approach is to express the enzyme(s), lyse the microorganisms, and add the cell lysate. Yet another approach is to purify, or partially purify, the enzyme(s) from a lysate and add pure or partially pure enzyme(s) to the reaction. If multiple enzymes are required for a reaction, the enzymes can be expressed in one or several microorganisms, including expressing all enzymes within a single microorganism.

A further approach, which can be combined with the above approaches, is to immobilize enzyme(s) to a support (exemplary strategies are outlined in Datta et al. (2013) 3 Biotech. February; 3(1): 1-9). As outlined in Datta et al., and not intending to be limiting, enzymes, either singly or in combination, can, for example, be adsorbed to, or covalently or non-covalently attached to, or entrapped within, natural or synthetic polymers or inorganic supports, including aggregates of the enzyme(s) themselves. Once immobilized, the enzyme(s) and support can be dispersed into bulk solution or packed into beds, columns, or any number of similar approaches to interacting reaction solution with the enzymes. Since aeration is important for the DAAO reaction envisioned here, bubble columns or similar may be used for enzyme immobilization. As examples, reaction mixture can be flowed through a column of immobilized enzymes (flow reaction), added to a fixed bed or column of immobilized enzymes, allowed to react, and either removed from the bottom or top of the reaction vessel (plug flow), or added to dispersed immobilized enzymes and allowed to react then the immobilized enzymes removed by filtration, centrifugation, or similar (batch). Thus, any method for immobilization of the enzymes may be employed in the methods of the invention.

The DAAO, TA, and/or other reactions can occur in a buffer. Exemplary buffers commonly used in biotransformation reactions include Tris, phosphate, or any of Good's buffers, such as 2-(N-morpholino)ethanesulfonic acid (MES); N-(2-Acetamido)iminodiacetic acid (ADA); piperazine-N,N'-bis(2-ethanesulfonic acid) (PIPES); N-(2-Acetamido)-2-aminoethanesulfonic acid (ACES); β-Hydroxy-4-morpholinepropanesulfonic acid (MOPSO); cholamine chloride; 3-(N-morpholino)propanesulfonic acid (MOPS); N,N-Bis(2-hydroxyethyl)-2-aminoethanesulfonic acid (BES); 2-[[1,3-dihydroxy-2-(hydroxymethyl)propan-2-yl]amino]ethanesulfonic acid (TES); 4-(2-hydroxyethyl)-1-piperazineethanesulfonic acid (HEPES); 3-(Bis(2-hydroxyethyl)amino)-2-hydroxypropane-1-sulfonic acid (DIPSO);

acetamidoglycine, 3-(N-Tris(hydroxymethyl)methylamino(-2-hydroxypropanesulfonic acid (TAPSO); Piperazine-N, N'-bis(2-hydroxypropanesulfonic acid) (POPSO); 4-(2-Hydroxyethyl)piperazine-1-(2-hydroxypropanesulfonic acid) (HEPPSO); 3-[4-(2-Hydroxyethyl)-1-piperazinyl]propane-sulfonic acid (HEPPS); tricine; glycinamide; bicine; or 3-[[1,3-dihydroxy-2-(hydroxymethyl)propan-2-yl]amino] propane-1-sulfonic acid (TAPS). Additional exemplary buffer recipes can be found in Whittall, J. and Sutton, P. W. (eds) (2012) Front Matter, in Practical Methods for Biocatalysis and Biotransformations 2, John Wiley & Sons, Ltd, Chichester, UK. In some embodiments, ammonium can act as a buffer. One or more organic solvents can also be added to the reaction.

Surprisingly, the DAAO, TA, and/or other reactions can occur with no or low levels (less than 1 mM) of buffer added (other than ammonium that may optionally be present due to addition of racemic glufosinate ammonium). In particular, immobilized DAAO and TA may be stable and active in the presence of less than 1 mM phosphate buffer and with no other buffer except any ammonium present due to the addition of racemic glufosinate ammonium.

The racemic glufosinate starting material can be provided in a number of forms. Various salts of racemic glufosinate, such as ammonium and hydrochloride, or the zwitterion, can be used. The racemic glufosinate may be in the form of a solid powder (such as a powder of greater than 80%, 85%, 90%, or 95% purity) or an aqueous solution (such as a roughly 50% solution of racemic glufosinate).

In some embodiments, the reaction occurs within a defined pH range, which can be between pH 4 to pH 10 (e.g., between pH 6 and pH 9, such as approximately pH 7.5 to pH 8).

In some embodiments, the reaction occurs at a defined temperature. The temperature can be kept at a point between room temperature and the boiling point of the solvent, most typically between room temperature and 50° C.

As indicated, the methods described herein provide a composition of substantially pure L-glufosinate (rather than a racemic mixture of L-glufosinate and D-glufosinate). Substantially pure L-glufosinate means that greater than about 70%, greater than about 75%, greater than about 80%, greater than about 85%, greater than about 90%, greater than about 95%, greater than about 96%, greater than about 97%, greater than about 98%, or greater than about 99% of the D-glufosinate has been converted to L-glufosinate resulting in a composition having greater than about 80%, greater than about 85%, greater than about 90%, greater than about 95%, greater than about 96%, greater than about 97%, greater than about 98%, or greater than about 99% L-glufosinate compared to the sum of the D-glufosinate and the L-glufosinate present in the composition.

In one embodiment, the L-glufosinate is not isolated from the biotransformation mixture and a composition comprising D-glufosinate, PPO, and L-glufosinate is obtained. This composition will contain at least 80% L-glufosinate by weight of the sum of L-glufosinate, D-glufosinate, and PPO, at least 90% L-glufosinate by weight of the sum of the components. This composition may be used directly as a herbicidal composition or as an ingredient in a formulated herbicidal product.

Alternatively, some or all of the components other than L-glufosinate can be removed from the biotransformation mixture, the mixture optionally concentrated, and then the mixture can be used directly (and/or with the addition of various adjuvants) for the prevention or control of weeds. The biotransformation mixture, in some instances, can be used directly (and/or with the addition of various adjuvants) for the prevention or control of weeds.

Additional steps to further purify the L-glufosinate can be added. Such further purification and isolation methods include ion exchange, extraction, salt formation, crystallization and filtration; each may be used multiple times or in suitable combination. Enzymes can be removed by simple filtration if supported, or if free in solution by the use of ultrafiltration, the use of absorbants like celite, cellulose or carbon, or denaturation via various techniques known to those skilled in the art.

Ion exchange processes effect separation by selective adsorption of solutes onto resins chosen for this purpose. Because products and impurities must be dissolved in a single solution prior to adsorption, concentration of the purified product stream by evaporation or distillation prior to isolation is usually required. Examples of the use of ion exchange for purification are described by Schultz et al., and in EP0249188(A2).

Purification may be achieved by the formation of an insoluble salt of L-glufosinate by the addition of a suitable acid, including hydrochloric acid, sulfuric acid, phosphoric acid, nitric acid, acetic acid and the like. Similarly, the purification may be achieved by the addition of a suitable base to form an insoluble salt. Useful bases include hydroxides, carbonates, sulfates and phosphates of alkali metals or hydroxides, carbonates, sulfates and phosphates of alkali earth metals. Other bases which contain nitrogen may be used, including ammonia, hydroxylamine, isopropylamine, triethylamine, tributylamine, pyridine, 2-picoline, 3-picoline, 4-picoline, 2,4-lutidine, 2,6-lutidine, morpholine, N-methymorpholine, 1,8-diazabicyclo[5.4.0]undec-7-ene, and dimethylethanolamine. It may be advantageous to concentrate the mixture or to add a solvent (or both) to maximize yield and optimize purity of the desired salt. Solvents suitable for this purpose include those in which the solubility of the desired salt is very low (such solvents are often called "anti-solvents"). Salts of L-glufosinate can be transformed into forms of glufosinate suitable for formulation by standard methods known to those skilled in the art. Alternatively, the L-glufosinate can be isolated as a zwitterion.

U.S. Pat. No. 9,255,115 B2 describes how the hydrochloric acid salt of L-glufosinate can be converted to the zwitterionic form with a base such as sodium hydroxide or sodium methoxide and then crystallized from aqueous alcohol solvent to afford L-glufosinate in relatively high purity. This method has the advantage of producing crystalline L-glufosinate that is not hygroscopic and therefore maintains a higher purity compared to amorphous L-glufosinate when exposed to humidity over time.

Other salts of L-glufosinate are known in the art. U.S. Pat. Nos. 5,767,309 and 5,869,668 teach the use of chiral alkaloid bases to form diastereomeric salts with racemic glufosinate. Purification is achieved because the salt of L-glufosinate precipitates from solution in much larger quantity than the corresponding salt of D-glufosinate. Therefore this method could be used with the present invention to obtain L-glufosinate with high enantiomeric excess, if desired.

Optionally, purification may be achieved by first crystallizing one or more impurities, removing the impurities by filtration and then further purifying L-glufosinate from the resulting filtrate by forming a salt as previously described. This is advantageous if unreacted amine donor can be partially or completely isolated and used in subsequent reactions. Similarly, unreacted PPO that is partially or completely isolated may be recycled for use in subsequent reactions.

Extraction may be used to purify the product. DE 3920570 C2 describes a process in which excess glutamic acid (used as the amine donor) is precipitated by adjusting the solution pH to 3.7 to 4.2 with sulfuric acid. After filtering the glutamic acid, the filtrate pH is lowered to 1-2 whereupon other impurities are extracted into a solvent. After extraction and concentration, ammonia is added to the aqueous solution to a pH of 5-7 whereupon ammonium sulfate precipitates. The ammonium sulfate is removed by filtration and the resulting filtrate is concentrated to afford the ammonium salt of L-glufosinate.

Isolation of L-glufosinate or its salts may be desirable, for example, for the purpose of shipping solids to the location of formulation or use. Typical industrial methods of isolation may be used, for example, a filtration, centrifugation, etc. Isolated product often requires the removal of water, volatile impurities and solvents (if present) and typical industrial drying equipment may be used for this purpose. Examples of such equipment include ovens, rotating drum dryers, agitated dryers, etc. In some cases, it may be advantageous to use a spray dryer.

It is not necessary to produce a solid product after purification. This may be advantageous if the formulation of L-glufosinate is to occur at the same site used for L-glufosinate production. L-glufosinate and many of its salts are readily soluble in water, and water is a convenient liquid to use for formulating products. For example, the amine donor is isolated by filtration and the resulting filtrate is concentrated by distillation. The pH of the filtrate may be adjusted to a desirable value and the resulting solution may be used as is or blended with formulation ingredients. In another example, a slurry of L-glufosinate or one of its salts may be prepared as described above and isolated by filtration. The solid could be dissolved directly on the filter by adding water or a suitable solvent to obtain a solution of L-glufosinate.

II. Compositions

Also described herein are compositions comprising the reaction products described above. In some embodiments, the composition substantially includes L-glufosinate and acceptable cationic or anionic salt forms such as the hydrochloride, ammonium, or isopropylammonium salts. In some embodiments, the composition comprises a mixture of L-glufosinate, PPO, and D-glufosinate.

Optionally, L-glufosinate is the predominant compound among L-glufosinate, PPO, and D-glufosinate. For example, L-glufosinate can be present in the composition in an amount of at least 80% by weight of the sum of L-glufosinate, PPO, and D-glufosinate, at least 85% by weight of the sum of L-glufosinate, PPO, and D-glufosinate, at least 90% by weight of the sum of L-glufosinate, PPO, and D-glufosinate, at least 95% by weight of the sum of L-glufosinate, PPO, and D-glufosinate, at least 96% by weight of the sum of L-glufosinate, PPO, and D-glufosinate, at least 97% by weight of the sum of L-glufosinate, PPO, and D-glufosinate, at least 98% by weight of the sum of L-glufosinate, PPO, and D-glufosinate, or at least 99% by weight of the sum of L-glufosinate, PPO, and D-glufosinate.

The composition can include PPO in an amount up to 20% by weight of the sum of L-glufosinate, PPO, and D-glufosinate. Optionally, the composition includes from 0.001% to 20% PPO (e.g., from 0.05% to 15% or from more than 0.01% to less than 5% PPO). For example, the composition can include PPO in an amount of less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, less than 0.1%, or less than 0.01% by weight of the sum of the masses of L-glufosinate, PPO, and D-glufosinate.

D-Glufosinate can be present in the composition in an amount of 15% or less by weight of the sum of L-glufosinate, PPO, and D-glufosinate. For example, D-glufosinate can be present in an amount of 14% or less, 13% or less, 12% or less, 11% or less, 10% or less, 9% or less, 8% or less, 7% or less, 8% or less, 6% or less, 5% or less, 4% or less, 3% or less, 2% or less, 1% or less, or 0.5% or less by weight of the sum of L-glufosinate, PPO, and D-glufosinate.

In some embodiments, the composition can contain small amounts (e.g., about 10% or less, about 8% or less, about 5% or less, about 2% or less, or about 1% or less by weight of the composition) of D-glufosinate. In some embodiments, the composition can contain small amounts (e.g., about 15% or less, about 10% or less, about 8% or less, about 5% or less, about 2% or less, or about 1% or less by weight of the composition) of PPO.

The compositions described herein are useful for application to a field of crop plants for the prevention or control of weeds. The composition may be formulated as a liquid for spraying on a field. The L-glufosinate is provided in the composition in effective amounts. As used herein, effective amount means from about 10 grams active ingredient per hectare to about 1,500 grams active ingredient per hectare, e.g., from about 50 grams to about 400 grams or from about 100 grams to about 350 grams. In some embodiments, the active ingredient is L-glufosinate. For example, the amount of L-glufosinate in the composition can be about 10 grams, about 50 grams, about 100 grams, about 150 grams, about 200 grams, about 250 grams, about 300 grams, about 350 grams, about 400 grams, about 500 grams, about 550 grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250 grams, about 1,300 grams, about 1,350 grams, about 1,400 grams, about 1,450 grams, or about 1,500 grams L-glufosinate per hectare.

The herbicidal compositions (including concentrates which require dilution prior to application to the plants) described herein contain L-glufosinate (i.e., the active ingredient), optionally some residual D-glufosinate and/or PPO, and one or more adjuvant components in liquid or solid form.

The compositions are prepared by admixing the active ingredient with one or more adjuvants, such as diluents, extenders, carriers, surfactants, organic solvents, humectants, or conditioning agents, to provide a composition in the form of a finely-divided particulate solid, pellet, solution, dispersion, or emulsion. Thus, the active ingredient can be used with an adjuvant, such as a finely-divided solid, a liquid of organic origin, water, a wetting agent, a dispersing agent, an emulsifying agent, or any suitable combination of these. From the viewpoint of economy and convenience, water is the preferred diluent. However, not all the compounds are resistant to hydrolysis and in some cases this may dictate the use of non-aqueous solvent media, as understood by those of skill in the art.

Optionally, one or more additional components can be added to the composition to produce a formulated herbicidal composition. Such formulated compositions can include L-glufosinate, carriers (e.g., diluents and/or solvents), and other components. The formulated composition includes an effective amount of L-glufosinate. Optionally, the L-glufosinate can be present in the form of L-glufosinate ammonium. The L-glufosinate ammonium can be present in an amount ranging from 10% to 30% by weight of the formulated composition. For example, the L-glufosinate ammonium can be present in an amount of 10%, 12%, 14%, 16%, 18%, 20%, 22%, 24%, 26%, 28%, or 30% by weight of the formulated composition. Optionally, the L-glufosinate ammonium is present in an amount of 12.25% or of 24.5%

In some examples, the formulated composition can include one or more surfactants. A suitable surfactant for use in the formulated composition includes sodium alkyl ether sulfate. The surfactant can be present in an amount from 10% to 40% by weight of the formulated composition. For example, the surfactant can be present in an amount of 10%, 12%, 14%, 16%, 18%, 20%, 22%, 24%, 26%, 28%, 30%, 32%, 34%, 36%, 38%, or 40% by weight of the formulated composition. Optionally, the sodium alkyl ether sulfate is present in an amount of 11.05%, 15.8%, 22.1%, or 31.6%.

The formulated composition can optionally include one or more solvents (e.g., organic solvents). Optionally, the solvent can be 1-methoxy-2-propanol, dipropylene glycol, ethylene glycol, and mixtures thereof. The one or more solvents can be present in an amount ranging from 0.5% to 20% by weight of the formulated composition. For example, the total amount of solvents in the composition can be present in an amount of 0.5% to 18%, 5% to 15%, or 7.5% to 10% by weight of the formulated composition.

Optionally, the solvent includes a combination of two solvents. For example, the solvents in the formulation can include 1-methoxy-2-propanol and dipropylene glycol. The 1-methoxy-2-propanol can be present, for example, in an amount of 0.5% to 2% by weight of the formulated composition. For example, the 1-methoxy-2-propanol can be present in the amount of 0.5%, 0.6%, 0.7%, 0.8%, 0.9%, 1.0%, 1.1% 1.2%, 1.3%, 1.4%, 1.5%, 1.6%, 1.7%, 1.8%, 1.9%, or 2.0% by weight of the formulated composition. Optionally, the 1-methoxy-2-propanol is present in an amount of 0.5% or 1.0% by weight of the formulated composition. The dipropylene glycol can be present in an amount of from 4% to 18% by weight of the formulated composition. For example, the dipropylene glycol can be present in an amount of 4%, 6%, 8%, 10%, 12%, 14%, 16%, or 18% by weight of the formulated composition. Optionally, the dipropylene glycol is present in an amount of 4.3% or 8.6% by weight of the formulated composition.

The formulated composition can also include one or more polysaccharide humectants. Examples of suitable polysaccharide humectants include, for example, alkyl polysaccharides, pentoses, high fructose corn syrup, sorbitol, and molasses. The polysaccharide humectant, such as alkyl polysaccharide, can be present in the formulated composition in an amount ranging from 4% to 20% by weight of the formulated composition. For example, the total amount of polysaccharide humectant in the composition can be present in an amount of 4% to 18%, 4.5% to 15%, or 5% to 10% by weight of the formulated composition. In some examples, the total amount of polysaccharide humectant, such as the alkyl polysaccharide, present in the formulated composition can be 40% 5%, 6%, 70%, 8%, 90%, 10%, 110%12%, 13%, 140%, 150%, 160%, 17%, or 18%. Optionally, the alkyl polysaccharide can be present in an amount of 3.2%, 4.9%, 6.2%, or 9.8%.

A diluent can also be included in the formulated composition. Suitable diluents include water and other aqueous components. Optionally, the diluents are present in an amount necessary to produce compositions ready for packaging or for use.

In one example, the formulated composition includes L-glufosinate ammonium in an amount of 12.25% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 36.75% by weight of the formulation.

In another example, the formulated composition includes L-glufosinate ammonium in an amount of 24.5% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 36.75% by weight of the formulation.

In another example, the formulated composition includes L-glufosinate ammonium in an amount of 12.25% by weight of the formulation; sodium alkyl ether sulfate in an amount of 15.8% by weight of the formulation; 1-methoxy-2-propanol in an amount of 0.5% by weight of the formulation; dipropylene glycol in an amount of 4.3% by weight of the formulation; alkyl polysaccharide in an amount of 4.9% by weight of the formulation; and water in an amount of 62.25% by weight of the formulation.

In another example, the formulated composition includes L-glufosinate ammonium in an amount of 24.5% by weight of the formulation; sodium alkyl ether sulfate in an amount of 22.1% by weight of the formulation; 1-methoxy-2-propanol in an amount of 1% by weight of the formulation; alkyl polysaccharide in an amount of 6.2% by weight of the formulation; and water in an amount of 46.2% by weight of the formulation.

In another example, the formulated composition includes L-glufosinate ammonium in an amount of 12.25% by weight of the formulation; sodium alkyl ether sulfate in an amount of 22.1% by weight of the formulation; 1-methoxy-2-propanol in an amount of 1% by weight of the formulation; alkyl polysaccharide in an amount of 6.2% by weight of the formulation; and water in an amount of 58.45% by weight of the formulation.

In another example, the formulated composition includes L-glufosinate ammonium in an amount of 12.25% by weight of the formulation; sodium alkyl ether sulfate in an amount of 11.05% by weight of the formulation; 1-methoxy-2-propanol in an amount of 0.5% by weight of the formulation; alkyl polysaccharide in an amount of 3.1% by weight of the formulation; and water in an amount of 73.1% by weight of the formulation.

Further components suitable for use in the formulated compositions provided herein are described in U.S. Pat. Nos. 4,692,181 and 5,258,358, both of which are incorporated by reference herein in their entireties.

The herbicidal compositions described herein, particularly liquids and soluble powders, can contain as further adjuvant components one or more surface-active agents in amounts sufficient to render a given composition readily dispersible in water or in oil. The incorporation of a surface-active agent into the compositions greatly enhances their efficacy. Surface-active agent, as used herein, includes wetting agents, dispersing agents, suspending agents, and emulsifying agents are included therein. Anionic, cationic, and non-ionic agents can be used with equal facility.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum solfonates, sulfonated vegetable oils, ditertiary acetylenic glycols, polyoxyethylene derivatives of alkylphenols (particularly isooctylphenol and nonylphenol), and polyoxyethylene derivatives of the mono-higher fatty acid esters of hexitol anhydrides (e.g. sorbitan). Exemplary dispersants include methyl cellulose, polyvinyl alcohol, sodium lignin sulfonates, polymeric alkyl naphthalene sulfonates, sodium naphthalene sulfonate, polymethylene bisnaphthalenesulfonate, and sodium N-methyl-N— (long chain acid) laurates.

Water-dispersible powder compositions can be made containing one or more active ingredients, an inert solid extender, and one or more wetting and dispersing agents. The inert solid extenders are usually of mineral origin, such as the natural clays, diatomaceous earth, and synthetic minerals derived from silica and the like. Examples of such extenders include kaolinites, attapulgite clay, and synthetic magnesium silicate. Water-dispersible powders described herein can optionally contain from about 5 to about 95 parts by weight of active ingredient (e.g., from about 15 to 30 parts by weight of active ingredient), from about 0.25 to 25 parts by weight of wetting agent, from about 0.25 to 25 parts by weight of dispersant, and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by dissolution or by mixing together and grinding an aqueous slurry of a water-insoluble active ingredient in the presence of a dispersing agent to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient described herein include hydrocarbons and water-immiscible ethers, esters, or ketones. The emulsifiable oil compositions generally contain from about 5 to 95 parts active ingredient, about 1 to 50 parts surface active agent, and about 4 to 94 parts solvent, all parts being by weight based on the total weight of emulsifiable oil.

Compositions described herein can also contain other additaments, for example, fertilizers, phytotoxicants and plant growth regulants, pesticides, and the like used as adjuvants or in combination with any of the above-described adjuvants. The compositions described herein can also be admixed with the other materials, e.g., fertilizers, other phytotoxicants, etc., and applied in a single application.

In each of the formulation types described herein, e.g., liquid and solid formulations, the concentration of the active ingredients are the same.

In some embodiments, the composition can include α-ketoglutarate as the major component. α-ketoglutarate is an important dicarboxylic acid and one of the key intermediates in the tricarboxylic acid cycle and amino acid metabolism. α-ketoglutarate can be isolated from the reaction mixture by methods such as that set forth in French Patent No. 07199, herein incorporated by reference. The α-ketoglutarate composition can be formulated with pharmaceutical excipients and carriers, food additives, or components used to form biomaterials. The α-ketoglutarate composition can be used in a variety of applications, including in synthesizing pharmaceutical agents, food additives, and biomaterials, as described in Li et al., *Bioprocess Biosyst Eng*, 39:967-976 (2016).

It is recognized that the herbicidal compositions can be used in combination with other herbicides. The herbicidal compositions of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vemolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, aminocyclopyrachlor, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compositions of the present invention can, further, be used in conjunction with glyphosate or 2,4-D on glyphosate-tolerant or 2,4-D-tolerant crops. It is generally preferred to use the compositions of the invention in combination with herbicides that are selective for the crop being treated and which complement the spectrum of weeds controlled by these compositions at the application rate employed. It is further generally preferred to apply the compositions of the invention and other complementary herbicides at the same time, either as a combination formulation or as a tank mix.

III. Methods of Use of L-Glufosinate Compositions

The compositions described herein can be used in methods for selectively controlling weeds in a field or any other area, including, for example, a railway, lawn, golf course, and others where the control of weeds is desired. Optionally, the field or other area can contain a crop of planted seeds or crops that are resistant to glufosinate. The methods can include applying an effective amount of a composition comprising L-glufosinate as described herein to the field.

The compositions described herein are useful for application to a field of crop plants for the prevention or control of weeds. The composition may be formulated as a liquid for spraying on a field. The L-glufosinate is provided in the composition in effective amounts. As used herein, effective amount means from about 10 grams active ingredient per hectare to about 1,500 grams active ingredient per hectare, e.g., from about 50 grams to about 400 grams or from about 100 grams to about 350 grams. In some embodiments, the active ingredient is L-glufosinate. For example, the amount of L-glufosinate in the composition can be about 10 grams, about 50 grams, about 100 grams, about 150 grams, about 200 grams, about 250 grams, about 300 grams, about 350 grams, about 400 grams, about 500 grams, about 550 grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250 grams, about 1,300 grams, about 1,350 grams, about 1,400 grams, about 1,450 grams, or about 1,500 grams L-glufosinate per hectare.

IV. Exemplary Embodiments

Non-limiting embodiments include:

1. A method for making L-glufosinate, comprising:

reacting D-glufosinate with a D-amino acid oxidase (DAAO) enzyme to form PPO (2-oxo-4-(hydroxy(methyl)phosphinoyl)butyric acid); and aminating the PPO to L-glufosinate by a transaminase (TA) enzyme, using an amine group from one or more amine donors, wherein at least 70% of the D-glufosinate is converted to L-glufosinate.

2. The method of embodiment 1, wherein the amine donor is selected from the group consisting of glutamate, L-glutamate, alanine, sec-butylamine, phenylethylamine, glycine, lysine, valine, serine, glutamine, isopropylamine, ethanolamine, 2-aminobutyric acid, and diaminoproprionic acid, or any secondary amine or amino acid.

3. The method of embodiment 1, wherein the D-glufosinate is originally present in a racemic mixture of D- and L-glufosinate or salts thereof.

4. The method of embodiment 1, wherein the DAAO enzyme is selected from the enzyme from *Rhodosporidium toruloides* or *Trigonopsis variabilis, Neolentinus lepideus, Trichoderma reesei,* or *Trichosporon oleaginosus*. In an embodiment, the *Rhodosporidium toruloides* DAAO enzyme is UniProt P80324. In an embodiment, the *Trigonopsis variabilis* DAAO enzyme is UniProt Q99042. In an embodiment, the *Neolentinus lepideus* DAAO enzyme is KZT28066.1. In an embodiment, the *Trichoderma reesei* DAAO enzyme is XP_006968548.1. In an embodiment, the *Trichosporon oleaginosus* DAAO enzyme is KLT40252.1.

5. The method of embodiment 1, wherein the DAAO enzyme is a mutant DAAO.

6. The method of embodiment 5, wherein the mutant DAAO is a mutant DAAO based on the sequence from *Rhodosporidium toruloides*.

7. The method of embodiment claim 5, wherein the mutant DAAO comprises one or more mutations at positions 54, 56, 58, 213, and 238.

8. The method of embodiment 7, wherein the mutation at position 54 is selected from the group consisting of N54C, N54L, N54T, and N54V.

9. The method of embodiment 7, wherein the mutation at position 56 is T56M.

10. The method of embodiment 7, wherein the mutation at position 58 is selected from the group consisting of F58A, F58G, F58H, F58K, F58N, F58Q, F58R, F58S, and F58T.

11. The method of embodiment 7, wherein the mutation at position 213 is M213S.

12. The method of embodiment 5, wherein the mutant DAAO comprises mutations F58K and M213S.

13. The method of embodiment 5, wherein the mutant DAAO comprises mutations at positions 54 and 56.

14. The method of embodiment 5, wherein the mutant DAAO comprises mutations N54T and T56M.

15. The method of embodiment 5, wherein the mutant DAAO comprises mutations F58Q or F58H.

16. The method of embodiment 5, wherein the mutant DAAO comprises mutations N54V and F58Q.

17. The method of embodiment 5, wherein the mutant DAAO comprises mutations N54V, F58Q, and M213S.

18. The method of embodiment 1, wherein the TA enzyme is a gabT transaminase from *Escherichia coli*. In an embodiment, the *Escherichia coli* gabT transaminase is UniProt P22256.

19. The method of embodiment 1, wherein the TA enzyme is encoded by SEQ ID NO: 1.

20. The method of embodiment 1, wherein the reacting step and the aminating step are performed in a single container.

21. The method of embodiment 20, wherein all reagents are substantially added at the start of the reaction.

22. The method of embodiment 20, wherein the reagents for the reacting step and the reagents for the aminating step are added to the single container at different times.

23. The method of embodiment 1, wherein the reacting step and the aminating step are performed in separate containers.

24. A composition comprising D-glufosinate, PPO, and L-glufosinate.

25. The composition of embodiment 24, wherein the amount of L-glufosinate is 90% or greater based on the total amount of D-glufosinate, PPO, and L-glufosinate.

26. The method of embodiment 1 wherein a solid is obtained having the composition of embodiment 24 or 25.

27. The method of embodiment 1 wherein a solution of L-glufosinate is obtained for use in a formulation which has herbicidal activity.

28. A formulation, comprising L-glufosinate ammonium in an amount from 10-30% by weight of the formulation; one or more additional components selected from the group consisting of sodium alkyl ether sulfate in an amount from 10-40% by weight of the formulation; 1-methoxy-2-propanol in an amount from 0.5-2% by weight of the formulation; dipropylene glycol in an amount from 4-18% by weight of the formulation; and alkyl polysaccharide in an amount from 4-20% by weight of the formulation; and water as the balance of the formulation.

29. The composition of embodiment 28, wherein the formulation comprises: L-glufosinate ammonium in an amount of 12.25% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 36.75% by weight of the formulation.

30. The composition of embodiment 28, wherein the formulation comprises: L-glufosinate ammonium in an amount of 24.5% by weight of the formulation; sodium alkyl ether sulfate in an amount of 31.6% by weight of the formulation; 1-methoxy-2-propanol in an amount of 1% by weight of the formulation; dipropylene glycol in an amount of 8.6% by weight of the formulation; alkyl polysaccharide in an amount of 9.8% by weight of the formulation; and water in an amount of 24.5% by weight of the formulation.

31. The composition of embodiment 28, wherein the formulation comprises: L-glufosinate ammonium in an amount of 12.25% by weight of the formulation; sodium alkyl ether sulfate in an amount of 15.8% by weight of the formulation; 1-methoxy-2-propanol in an amount of 0.5% by weight of the formulation; dipropylene glycol in an amount of 4.3% by weight of the formulation; alkyl polysaccharide in an amount of 4.9% by weight of the formulation; and water in an amount of 62.25% by weight of the formulation.

32. A formulation, comprising L-glufosinate ammonium in an amount from 10-30% by weight of the formulation; one or more additional components selected from the group consisting of sodium alkyl ether sulfate in an amount from 10-40% by weight of the formulation; 1-methoxy-2-propanol in an amount from 0.5-2% by weight of the formulation; and alkyl polysaccharide in an amount from 3-10% by weight of the formulation; and water as the balance of the formulation.

33. The composition of embodiment 32, wherein the formulation comprises: L-glufosinate ammonium in an amount of 12.25% by weight of the formulation; sodium alkyl ether sulfate in an amount of 22.1% by weight of the formulation; 1-methoxy-2-propanol in an amount of 1% by weight of the formulation; alkyl polysaccharide in an amount of 6.2% by weight of the formulation; and water in an amount of 58.45% by weight of the formulation.

34. The composition of embodiment 32, wherein the formulation comprises: L-glufosinate ammonium in an amount of 24.5% by weight of the formulation; sodium alkyl ether sulfate in an amount of 22.1% by weight of the formulation; 1-methoxy-2-propanol in an amount of 1% by weight of the formulation; alkyl polysaccharide in an amount of 6.2% by weight of the formulation; and water in an amount of 46.2% by weight of the formulation.

35. The composition of embodiment 32, wherein the formulation comprises: L-glufosinate ammonium in an amount of 12.25% by weight of the formulation; sodium alkyl ether sulfate in an amount of 11.05% by weight of the formulation; 1-methoxy-2-propanol in an amount of 0.5% by weight of the formulation; alkyl polysaccharide in an amount of 3.1% by weight of the formulation; and water in an amount of 73.1% by weight of the formulation.

36. A method for selectively controlling weeds in an area comprising:
applying an effective amount of a composition comprising L-glufosinate at an enantiomeric excess of greater than 90% over D-glufosinate to the area.

37. The method of embodiment 36, wherein the amount of the composition is applied at less than 400 grams of the sum of L-glufosinate and D-glufosinate per hectare.

38. A method for selectively controlling weeds in an area comprising:
applying an effective amount of a composition comprising L-glufosinate at an enantiomeric excess of greater than 90% over D-glufosinate to the area and more than 0.01% but less than 10% PPO to the area.

39. The method of embodiment 38, wherein the amount of the composition is applied at less than 400 grams of the sum of L-glufosinate, D-glufosinate and PPO per hectare.

40. A method for selectively controlling weeds in an area containing a crop of planted seeds or crops that are resistant to glufosinate, comprising:
applying an effective amount of a composition comprising L-glufosinate at an enantiomeric excess of greater than 90% over D-glufosinate and more than 0.01% but less than 10% PPO to the field.

The following examples are offered by way of illustration and not by way of limitation.

EXAMPLES

Example 1: DAAO Enzyme Purification

The coding sequence of a mutant DAAO from *Rhodosporidium toruloides* (for example, consisting of a MMARIRL leader sequence and the F58K and M213S mutations) was cloned into the pET14b vector to allow for expression of an N terminally 6×His tagged protein. This pET14b-RgDAAO plasmid was transformed into BL21 (BE3) trxB pLysS cells. The sequence of the wild type DAAO from *Rhodosporidium toruloides* to which all numbering described here corresponds, is:

(SEQ ID NO: 2)
MHSQKRVVVLGSGVIGLSSALILARKGYSVHILARDLPEDVSSQTF

ASPWAGANWTPFMTLTDGPRQAKWEESTFKKWVELVPTGHAMWLKG

TRRFAQNEDGLLGHWYKDITPNYRPLPSSECPPGAIGVTYDTLSVH

APKYCQYLARELQKLGATFERRTVTSLEQAFDGADLVVNATGLGAK

SIAGIDDQAAEPIRGQTVLVKSPCKRCTMDSSDPASPAYIIPRPGG

EVICGGTYGVGDWDLSVNPETVQRILKHCLRLDPTISSDGTIEGIE

VLRHNVGLRPARRGGPRVEAERIVLPLDRTKSPLSLGRGSARAAKE

KEVTLVHAYGFSSAGYQQSWGAAEDVAQLVDEAFQRYHGAARESKL.

To purify DAAO enzyme, cells were grown in 400 mL autoinducing medium (LB broth base with trace elements, Formedium) at 30° C. for 20 to 24 hours. Cells were harvested in precooled centrifuges and buckets, washed with cold water, centrifuged again, and stored at −80° C. until purification.

Cell pellets were then thawed in lysis buffer (50 mM potassium phosphate, pH 8.0, 20 mM imidazole and 1% Sigma protease inhibitor cocktail (PIC) w/o EDTA) at a volume of 5 mL of lysis buffer per 1 g cell pellet. While on ice, cells were sonicated 4 times for 30 seconds at an amplitude of 10. The cell lysate was clarified by centrifugation and then added to cobalt resin (HisPur Cobalt, ThermoScientific) at 4 times the bed volume. The cell lysate was incubated for 1 hour, with gentle shaking, at room temperature. The resin was added to a column and washed twice with 5 bed volumes of wash buffer (50 mM Kpi, pH 8.0, 20 mM imidazole). The elution was performed 4 times with 1 bed volume of elution buffer (50 mM Kpi, 200 mM imidazole).

Example 2: Colorimetric Determination of DAAO Activity

DAAO activity was determined similarly to Berneman et al. In brief, 100 uL of substrate and HRP (0.1 mg/mL HRP, Sigma P8375, and the desired amount of D-glufosinate or racemic D/L-glufosinate in 50 mM potassium phosphate, pH 8) was added to a Brand UV micro cuvette. To that, 50 uL of dyes (60 ug/mL TBHBA, Sigma 439533, and 1 mg/mL 4-aminoantipyrine, Sigma A4382, in 50 mM potassium phosphate, pH 8) was added and then 50 uL of enzyme mix (DAAO concentration as desired in 100 mM potassium phosphate, pH 8). The reaction was monitored on a spectrophotometer at 510 nm over an appropriate time to determine the enzyme kinetics. Although no flavin adenine dinucleotide (FAD) was added to the purification of DAAO or the reaction, this reagent can optionally be included. Two exemplary mutant variants of *Rhodosporidium toruloides* DAAO, AC201 (containing F58K and M213 S) and AC263 (containing N54T, T56M, F58K, and M213S), purified as in Example 1, were tested using this assay and shown to produce hydrogen peroxide, demonstrating their activity in oxidizing D-glufosinate. AC201 and AC263 have similar Vmax, but AC263 has a lower K.

Example 3: Purification of Transaminases

To purify, for example, the *Escherichia coli* gabT transaminase (UniProt P22256), the gene was amplified from *E. coli* K12 strain ER2925 and cloned into pET-14b to generate an N-terminal 6×His tagged version. This plasmid was then transformed into BL21 (DE3) cells for induction. After induction in autoinducing media, cells were lysed by sonication and the 6×His tagged enzyme purified as described in Example 1.

Example 4: Demonstration of Transaminase Activity

In a non-limiting example, the source of PPO for a transamination assay can be D-glufosinate or racemic D/L-glufosinate that has been converted by a DAAO to PPO. In the first step, 39 mM racemic D/L-glufosinate was incubated with 0.5 mg/ml purified *Rhodosporidium toruloides* DAAO F58K M213S and 10 ug/mL catalase in 50 mM Potassium phosphate buffer, pH8 for 20 hours at 30 C. This resulted in conversion of the majority of the D-glufosinate to PPO. Subsequently, purified *E. coli* gabT was added at 20 ug/mL and L-glutamate was added at 50 mM as the amine donor. At relevant points, samples were stopped by boiling for 10 minutes followed by precipitation with an equal volume of acetonitrile. The individual chemical species were resolved on an IPLC with a Chirobiotic T2 column and quantified by comparison to authentic standards.

The combination of a mutant variant of DAAO and a transaminase resulted in an improvement of an enantiomeric enrichment that started at 0% for L-glufosinate over D-glufosinate (i.e., equal representation of D-glufosinate and L-glufosinate) to an enantiomeric enrichment of 92%. These results demonstrate that *E. coli* gabT has transaminase activity, and this assay can be used to determine the activity of any number of wild type and/or mutant potential transaminases.

Example 5: De-Racemization of Racemic D/L-Glufosinate in a Single Vessel

Reactions were set up similarly as in Example 4. The system (5.45 mL, 30° C.) was run in phosphate buffer at a pH of 7.3. It was noted that 50 mM of phosphate buffer at a pH of 8.0 was inadequate to buffer the amino acid additions and that the unadjusted pH after amino acid additions in this system was pH 6.4. The pH was adjusted using 1M of the base salt K2HPO4 to a volume of 5.45 mL, meaning that the actual initial substrate concentration by addition was 275 mM. The following reagents were added essentially simultaneously at the start of the reaction: 271 mg D,L-glufosinate, 420 mg glutamate, 15 mg AC263 DAAO, 50 µg catalase, and 1.0 mg *E. coli* gab T transaminase. FIG. 2 shows that, when all reagents were added, the amount of D-PPT (D-glufosinate) diminished with only modest accumulation of PPO. This result indicates an efficient deracemisation of D/L-glufosinate into L-glufosinate by the RgDAAO/EcgabT enzyme couple.

Example 6: Demonstration of Improved DAAO Enzymes

Using protein mutagenesis strategies as outlined above, improved and variant DAAO enzymes were identified. The enzymes were assayed according to the procedures described below.

Stock Solutions:
The following dye stock solutions were prepared: a 20 mg/mL stock solution of 2,4,6-tribromo-3-hydroxybenzoic acid (TBHBA) in DMSO; and a 100 mg/mL stock solution of 4-aminoantipyrine (4-AAP) in water. The following enzyme stock solution was prepared: a 1 mg/mL stock solution of horseradish peroxidase (HRP) type 6 in a pH 8.0 potassium phosphate buffer. The following substrate stock solution was prepared: varying concentrations of D or DL amino acid in a pH 8.0 potassium phosphate buffer.

Reaction Mixes:
The following reaction mixtures were prepared:
Mix A is a combination of the substrate and HRP enzyme. Solutions were prepared for each substrate concentration to be assayed using reaction buffer. The solutions were two times the final substrate concentration and 0.2 mg/mL for the HRP solution.

Mix B is a dye mixture. To 5 mL of reaction buffer was added 120 µL of TBHBA solution and 400 µL of 4-AAP solution.

Mix C is an enzyme mixture. A 0.1 mg/mL solution of DAAO in reaction buffer was prepared. The final reaction concentration was 25 µg/mL.

Protocol:
A spectrophotometer was used at a wavelength of 510 nm, which corresponds to the maximum absorbance for 4-AAP/TBHBA and is the point at which the extinction coefficient is 29400 $M^{-1}$ $cm^{-1}$. The temperature for performing the assays was 30° C. The reaction kinetics were obtained by measuring every minute for 15 minutes. Between measurements, 20 seconds of orbital shaking at normal intensity was performed, followed by 10 seconds of settling time.

Using a 96-well plate, the following mixes (with replicates) were added in the following order using multichannel: 100 µl mix A, 50p mix B, and 50 µl mix C. The measurements were started immediately after the enzyme addition.

The enzyme kinetics were measured as described above, plotted on a Michaelis Menten graph, and used to calculate Vmax and $K_M$. For the variant Ac302 (54V, 58Q, 213S), the Vmax was 4.2 umol/min*mg.

This analysis was completed for a number of variant DAAO enzymes as above except that the Mix C stock was 0.2 mg/mL solution of DAAO and this final reaction concentration of DAAO was 50 ug/mL.

As shown below in Table 1, variant mutant DAAO enzymes showed a range of activities:

TABLE 1

| Variant | Mutations | Vmax (% of Ac302) |
|---------|-----------|-------------------|
| Ac263 | 54T, 56M, 58K, 213S | 33 |
| Ac302 | 54V, 58Q, 213S | 100 |
| Ac305 | 54C, 58H, 213S | 88 |
| Ac309 | 54T, 58T, 213S | 71 |
| Ac312 | 54T, 58G, 213S | 74 |
| Ac314 | 54T, 58Q, 213S | 99 |
| Ac316 | 54T, 58S, 213S | 75 |
| Ac318 | 54T, 58A, 213S | 71 |
| Ac319 | 54L, 58R, 213S | 64 |
| Ac320 | 54V, 58R, 213S | 76 |
| Ac322 | 54V, 58N, 213S | 79 |

Example 7: De-Racemization of Racemic D/L-Glufosinate at a 5 L Reaction Size The scale of the de-racemization is increased using approaches familiar to those skilled in the art. Reagents and their relative ratios are substantially similar to Example 5, but the amounts are significantly greater. Rather than tubes in shakers, the reactions are performed in stirred jacketed reactors, including, optionally, air or oxygen sparging of the broth or headspace. These reactors vary in size, from less than 10 mL reaction to tens or hundreds of thousands of liters. Stirring rates are chosen to increase reaction mixing and rate while minimizing power consumption and shear.

In one example, the reaction was run at the 5 L scale. The system (5 L, 30° C.) was run in 200 mM phosphate buffer at a pH of 8.0 in a stirred, jacketed reactor. The following reagents were added essentially simultaneously at the start of the reaction: 300 mM D,L-glufosinate, 900 mM glutamate, 7.5 g AC302 DAAO, 0.2 g catalase, and 1.0 g $E.$ $coli$ gab T transaminase. In addition, 500 mL isopropanol was added to control foaming. During the course of the reaction, air was introduced at 0.3 VVM (volumes of air per volume of reaction mixture per minute).

HPLC analysis of the reaction demonstrated that equilibrium was reached within 8 hours, with the enantiomeric excess of L-glufosinate over D-glufosinate greater than 99% and the ratio of L-glufosinate to PPO 90% to 10%. This result indicates an efficient deracemisation of D/L-glufosinate into L-glufosinate by the RgDAAO/EcgabT enzyme couple at the larger scale.

Example 8: Impact of Oxygen on Reaction Rate

Although stirred, jacketed reactors or immobilized columns typically allow for some oxygen transfer, the rate of oxygen uptake afforded by passive aeration is not sufficient for an efficient process. In one example, a reaction was run in the same vessel as Example 7 under substantially the same conditions, but under reduced (0.01 VVM), with twice the AC302 DAAO on a volumetric basis (3 g/L versus 1.5 g/L), and without the isopropanol. In this case, the reaction took more than 60 hours to achieve equilibrium, demonstrating the critical importance of aeration for an efficient reaction.

Example 9: Co-Immobilization of DAAO and TA

DAAO and TA enzymes were co-immobilized on EziG controlled pore glass beads (EnginZyme). 100 mg of EziG type 3 beads were shaken at room temperature with 3 ml of solution containing 16 mg of purified AC302 DAAO and 1.6 mg of purified gabT in 50 mM potassium phosphate buffer pH 7.5, 0.5M NaCl, 20 mM imidazole in a 50 ml Falcon tube. After 30 minutes, beads were spun down, immobilizing solution was removed, and beads were washed 3 times with 10 ml of 100 mM potassium phosphate buffer pH 7.5.

The reaction was started by adding all other components to the washed beads. The reaction mix contained 300 mM D/L-glufosinate, 900 mM L-glutamic acid, 50 ug catalase, 198 mM potassium phosphate in 2.5 mL. The reaction was incubated at 30 C with shaking (250 rpm) in a 50 mL tube covered in parafilm with holes poked through for gas exchange.

After 1 hour, the depletion of D-glufosinate and formation of L-glufosinate was determined by HPLC and these rates calculated. After 6 hours, beads were spun down, reaction mixture was removed, and beads were washed 3 times with 10 ml of 100 mM Potassium Phosphate buffer pH 7.5. Beads were then stored at 4 C for 18 to 72 hours before the reaction was repeated, for a total of 15 times, after which the retained activity was greater than 50% of the initial activity.

Example 10: Effect of Buffer on Reaction

When soluble AC302 DAAO and $E.$ $coli$ gabT TA enzymes are used, phosphate buffer at >50 mM is required for full activity. A 100 mL reaction was incubated at 30 C with shaking (250 rpm) in a 500 mL flask covered in parafilm. An air pump was used to bubble air through the reaction for the first 5 hours. The air pump was removed for overnight incubation so the reaction would not bubble over and new parafilm with air holes was used for gas exchange. The reaction mix contained 300 mM D/L-glufosinate, 905 mM L-glutamic acid, 80 mg AC302 DAAO (0.8 mg/mL), 14.5 mg gabT (0.145 mg/mL), 2 mg catalase, and isopropanol as anti-foam reagent (10% initial concentration, isopropanol was additionally added at 2 hr (2 mL), 3 hr (1 mL), 3.5 hr (1 mL), and at 4 hr (2 mL)). 500 uL of iN NaOH (added before enzymes) was used to adjust pH from about 6 to about 7. pH remained at about 7 for the entire reaction without further adjustment. Due to the potassium phosphate in the stock enzyme buffer, the final mixture was 45 mM phosphate buffer. When compared to a similar reaction with 200 mM phosphate buffer, the reaction rate was 50-60% of that of the reaction with the 200 mM buffer.

When immobilized AC302 DOOA and $E.$ $coli$ gatT TA enzymes are used, phosphate buffer of less than 1 mM is sufficient for full activity. Immobilized proteins were prepared and reaction performed as in Example 9 for the "Buffered" reaction. In addition, immobilized proteins were prepared and reactions performed as in Example 9 for the "pH 7" reaction, except that sodium hydroxide was used to adjust the pH of the reaction to pH 7 and no phosphate buffer was added (residual phosphate buffer from the enzyme storage buffer is less than 1 mM). This work demonstrated that the initial reaction rate for both the DAAO and combined DAAO and gabT reactions are very similar with and without the addition of phosphate buffer when immobilized enzymes are used.

Example 11: Isopropylamine as an Amine Donor

Isopropylamine can be used as an amine donor for conversion of PPO to L-glufosinate with the use of an appropriate TA. PPO was converted to L-glufosinate in a reaction with the following components:

0.25 mg/mL TA encoded by SEQ ID NO: 1
25 mM PPO
0.2 mM pyridoxal phosphate
250 mM isopropylamine (pHed to 8 w/H3PO4)
100 mM Kphos buffer pH 8.0

The reaction was incubated at 25 to 30° C. for 30 hours with gentle shaking (250 rpm). At 0 hours, the amount of L-glufosinate as measured by HPLC was 0 mM, at 20 hours it was 14 mM, and at 30 hours it was 18 mM. This demonstrates that the enzyme encoded by SEQ ID NO: 1 can convert PPO into L-glufosinate.

Example 12: Lysine as an Amine Donor

Lysine can be used as an amine donor for conversion of PPO to L-glufosinate with the use of an appropriate TA. PPO was converted to L-glufosinate in a reaction with the following components:

0.4 mg/mL gabT (purified as in Example 3)
25 mM PPO (pHed to 8 w/NaOH)
0.2 mM pyridoxal phosphate
75 mM L-Lysine dihydrochloride (pHed to 8 w/NaOH)
100 mM Kphos buffer pH 8.0

The reaction was incubated at 30° C. for 20 hours with shaking (250 rpm). L-glufosinate was formed at a rate of 0.4 mM/hr over the 20 hours. This demonstrates that L-lysine can be used to convert PPO to L-glufosinate.

Example 13: Purification and Isolation of L-Glufosinate

Several batches prepared following the procedure described in Example 9 but at larger scale were generated. After the beads were removed, each batch was heated to 90° C. for at least 10 minutes, and after cooling to 20-25° C., filtered to remove a small amount of solids. To each individual batch was added 37% HCl, dropwise, to effect the precipitation of glutamic acid. The amount of 37% HCl added was approximately 10% of the volume of the batch. The resulting white solid was removed by filtration. The batches were combined and concentrated under vacuum to an oil; the oil contained approximately 153 grams of L-glufosinate. The oil was diluted with five volumes of water and 37% HCl was added to adjust the solution to pH 1. The solution was treated sequentially with two portions each of approximately 3.0 kg of prewashed DOWEX 50WX8 cation exchange resin. In each treatment, the solution was allowed to mix with the resin for 30 minutes after which the resin was isolated on a filter. Both portions of resins were combined and washed first with water and then eluted with 4M NH$_4$OH. The eluent was concentrated under vacuum to an oil; PPO and 2-oxoglutarate were not present in the oil. Approximately 100 grams of the oil was diluted with water and the aqueous ammonium hydroxide was added until the pH was approximately 9. To the batch was added 1.0 kg of prewashed DOWEX Monosphere (hydroxide form) anion exchange resin and the mixture was stirred for approximately 40 minutes. An equal amount of DOWEX Monosphere resin, prewashed, was charged to a glass column. The slurry of DOWEX resin in water was added to the column on top of the prewashed resin. 800 mL of water was charged to the column followed by 0.1 N acetic acid, which was kept flowing through the column until all of the glutamic acid had eluted as determined by HPLC. 4 N acetic acid was fed to the column until all of the L-glufosinate had eluted from the column as determined by IPLC. The solution of L-glufosinate was concentrated under vacuum. The resulting oil was diluted with water and concentrated under vacuum to minimum volume two times. Methanol was added until a clear solution was obtained and an equal volume of heptane was added. The mixture was concentrated under vacuum to minimum volume and the procedure was repeated. The remaining 168 grams of oil recovered from the cation exchange treatment was treated in a similar fashion to obtain an overall total of 108 grams of crude L-glufosinate. The ratio of L-glufosinate to glutamic acid was greater than 99:1 as determined by NMR. The resulting solid was mixed with aqueous ammonium hydroxide and concentrated to dryness to afford 111 grams of L-glufosinate ammonium. Neither methanol nor acetic acid was detected by NMR analysis of the product.

It is understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may be used in the practice or testing of the invention, representative illustrative methods and materials are now described.

SEQUENCES

```
SEQ ID NO: 1:
MNIAAQSWERREATSFFHTFTDLPSLKTDGPVIIDHGEGPYIIDTV

GRRYFEGNSGLWNMTLGFSERRLSDAALKQYQEFPGYHTFFGRNSK

PTVELAERMLKLAPAPMSRVFFTNSGSEANESIVKLLWMMWAAEGR

PERRKLLTRKNAYHGATVMASALTGKDYVKAFGLPGPEIVTLDCPH

AWRFALPGEGDDEFAARLAANLETRILQEGPETIAGMFAEPVMGAG

GVIVPPATYFAKIQPVLQRYGIPLIADEVICGFGRTGSLWGTLAVG
```

QQPDIIVASKSMSAGYFPMGAVMLSADIDKRATAASEVWEEFPHGF
TTGGHPVGCAISLEAIRIITEEGVFENVKSVSETFQSGLRALADHP
MIGEARGMGLMGALETVADKKTKQSFSGDLRIGERISKEARDRGFI
IRPLGSSVVLAPPFISTHGQIEELLAVLKEVLDVVYGTVKGEVA

SEQ ID NO: 2:
MHSQKRVVVLGSGVIGLSSALILARKGYSVHILARDLPEDVSSQTF
ASPWAGANWTPFMTLTDGPRQAKWEESTFKKWVELVPTGHAMWLKG
TRRFAQNEDGLLGHWYKDITPNYRPLPSSECPPGAIGVTYDTLSVH
APKYCQYLARELQKLGATFERRTVTSLEQAFDGADLVVNATGLGAK
SIAGIDDQAAEPIRGQTVLVKSPCKRCTMDSSDPASPAYIIPRPGG
EVICGGTYGVGDWDLSVNPETVQRILKHCLRLDPTISSDGTIEGIE
VLRHNVGLRPARRGGPRVEAERIVLPLDRTKSPLSLGRSARAAKE

KEVTLVHAYGFSSAGYQQSWGAAEDVAQLVDEAFQRYHGAARESKL

SEQ ID NO: 3:
MNSNKELMQRRSQAIPRGVGQIHPIFADRAENCRVWDVEGREYLDF
AGGIAVLNTGHLHPKVVAAVEAQLKKLSHTCFQVLAYEPYLELCEI
MNQKVPGDFAKKTLLVTTGSEAVENAVKIARAATKRSGTIAFSGAY
HGRTHYTLALTGKVNPYSAGMGLMPGHVYRALYPCPLHGISEDDAI
ASIHRIFKNDAAPEDIAAIVIEPVQGEGGFYASSPAFMQRLRALCD
EHGIMLIADEVQSGAGRTGTLFAMEQMGVAPDLTTFAKSIAGGFPL
AGVTGRAEVMDAVAPGGLGGTYAGNPIACVAALEVLKVFEQENLLQ
KANDLGQKLKDGLLAIAEKHPEIGDVRGLGAMIAIELFEDGDHNKP
DAKLTAEIVARARDKGLILLSCGPYYNVLRILVPLTIEDAQIRQGL
EIISQCFDEAKQ

---

What is claimed is:

1. A method for making L-glufosinate, comprising:
reacting D glufosinate with a D-amino acid oxidase (DAAO) enzyme to form PPO (2-oxo-4-(hydroxy (methyl)phosphinoyl)butyric acid) while aerating; and
aminating the PPO to L-glufosinate by an L-amino acid dehydrogenase (LAAD) enzyme in the presence of an ammonia source,
wherein at least 70% of the D-glufosinate is converted to L-glufosinate; and
wherein the method is performed ex vivo.

2. The method according to claim 1, wherein the D-glufosinate is originally present in a racemic mixture of D- and L-glufosinate or salts thereof.

3. The method according to claim 1, wherein the DAAO enzyme has the amino acid sequence of SEQ ID NO: 2.

4. The method of claim 1, wherein the DAAO enzyme is a mutant DAAO comprising one or more mutations at positions 54, 56, 58, 213, and 238, using SEQ ID NO: 2 as a reference sequence.

5. The method of claim 4, wherein the mutation at position 54 is selected from the group consisting of N54C, N54L, N54T, and N54V.

6. The method of claim 4, wherein the mutation at position 56 is T56M.

7. The method of claim 4, wherein the mutation at position 58 is selected from the group consisting of F58A, F58G, F58H, F58K, F58N, F58Q, F58R, F58S, and F58T.

8. The method of claim 4, wherein the mutation at position 213 is M213S.

9. The method of claim 4, wherein the mutant DAAO comprises mutations at positions 54 and 56, using SEQ ID NO: 2 as a reference sequence.

10. The method of claim 4, wherein the mutant DAAO comprises mutations F58Q or F58H, using SEQ ID NO: 2 as a reference sequence.

11. The method of claim 4, wherein the mutant DAAO comprises mutations N54V and F58Q, using SEQ ID NO: 2 as a reference sequence.

12. The method of claim 4, wherein the mutant DAAO comprises mutations N54V, F58Q, and M213S, using SEQ ID NO: 2 as a reference sequence.

13. The method of claim 1, wherein the reacting step and the aminating step are performed in a single container.

14. The method of claim 13, wherein all reagents are substantially added at the start of the reaction.

15. The method of claim 13, wherein the reagents for the reacting step and the reagents for the aminating step are added to the single container at different times.

16. The method of claim 1, wherein the reacting step and the aminating step are performed in separate containers.

17. The method of claim 1, wherein the aerating comprises introducing oxygen, oxygen enriched air, an oxygen enriched gas stream, or air.

18. The method of claim 1, wherein the aerating is conducted intermittently or continuously.

* * * * *